US007253151B2

(12) United States Patent
Sung et al.

(10) Patent No.: US 7,253,151 B2
(45) Date of Patent: Aug. 7, 2007

(54) GENES OF IL-12P40 SUBUNIT MUTATED FOR IMPROVING THE ACTIVITY OF IL-12 AND USE THEREOF FOR DNA VACCINE ADJUVANT

(75) Inventors: Young Chul Sung, Kyungsangbuk-do (KR); Sung Hee Lee, Seoul (KR); Sang Jun Ha, Kyungsangbuk-do (KR); Man Ki Song, Kyungsangbuk-do (KR); Jun Chang, Kyungsangbuk-do (KR)

(73) Assignee: Genexine Co., Ltd., Pohang (KR)

( * ) Notice: Subject to any disclaimer, the term of this patent is extended or adjusted under 35 U.S.C. 154(b) by 0 days.

(21) Appl. No.: 10/221,975

(22) PCT Filed: Mar. 15, 2001

(86) PCT No.: PCT/KR01/00408

§ 371 (c)(1),
(2), (4) Date: Apr. 29, 2003

(87) PCT Pub. No.: WO01/68802

PCT Pub. Date: Sep. 20, 2001

(65) Prior Publication Data

US 2004/0023332 A1    Feb. 5, 2004

(30) Foreign Application Priority Data

Mar. 15, 2000 (KR) ............... 2000-13133
Mar. 13, 2001 (KR) ............... 2001-12987

(51) Int. Cl.
| | |
|---|---|
| A01N 43/04 | (2006.01) |
| A01N 63/00 | (2006.01) |
| A01N 65/00 | (2006.01) |
| A61K 31/70 | (2006.01) |
| C12N 5/00 | (2006.01) |
| C12N 5/02 | (2006.01) |
| C12Q 1/68 | (2006.01) |
| A61K 38/24 | (2006.01) |
| A61K 38/27 | (2006.01) |
| C07K 1/00 | (2006.01) |
| C07K 14/00 | (2006.01) |
| C07K 16/00 | (2006.01) |
| C07K 17/00 | (2006.01) |

(52) U.S. Cl. ............... 514/44; 424/93.1; 435/325; 435/6; 536/23.5; 536/23.52; 530/399

(58) Field of Classification Search ............ 514/44; 424/93.1; 536/23.4, 23.1, 24.31; 530/350
See application file for complete search history.

(56) References Cited

U.S. PATENT DOCUMENTS 6,517,839 B1 * 2/2003 Modlin et al. .......... 424/190.1

OTHER PUBLICATIONS

Deonarain (1998) Exp. Opin. Ther. Pat., 8(1): 53-69.*
Gorecki (2001) Exp. Opin. Emerging Drugs, 6(2): 187-98.*
Verma, et al. (1997) Nature, 389: 239-42.*
Eck, et al. (1996) Goodman & Gilman's The Pharmacological Basis of Therapeutics, 9th Ed., McGraw-Hill, New York, NY., pp. 77-101.*
J. Rudinger (1976) Peptide Hormones, Ed. JA. Parsons, University Park Press, Baltimore, MD., pp. 1-7.*
Bowie, et al. (1990) Science, 247: 1306-10.*
Ha, et al. (2002) Nature Biotech., 20: 381-86.*
Accession. No. AAB62945 of GENEBANK, published Jul. 14, 1997, to Beyer, et al.*
Song, et al. (2000) J. Virol., 74(6): 2920-25.*
Masoumi, et al. (2003) Virus Research, 94: 113-120.*
Gubler, et al. (1991) Proc. Natl. Acad. Sci., USA., 88: 4143-47.*
Kim, et al. (1992) Molec. Cell. Biol., 12(8): 3636-43.*
Ohlman, et al. (1999) RNA, 5(6): 764-78.*
Rogozin, et al. (2001) Bioinformatics, 17(10): 890-900.*
Saiz, et al. (1999) Arch. Virol., 144: 215-29.*
Yap et al., J Immunol., Jul. 15, 2000; 165(2):628-31.
Stobie et al., Proc Natl Acad Sci USA, Jul. 18, 2000; 97(15):8427-32.
Gurunathan et al., J Immunol., Jul. 15, 2000; 165(2):915-24.
Lode et al., Proc Natl Acad Sci USA, Mar. 3, 1998; 95(5):2475-80.
Wang et al., Eur J Immunol., Jun. 1999; 29(6):2007-13.
Yoshimoto et al., J. Immunol., Jan. 15, 1998; 160(2):588-94.
Kieper et al., J Immunol., May 1, 2001; 166(9):5515-21.

* cited by examiner

*Primary Examiner*—Joseph Woitach
*Assistant Examiner*—Robert M. Kelly
(74) *Attorney, Agent, or Firm*—JHK Law

(57) ABSTRACT

The present invention relates to the IL-12p40 subunit mutant gene which can produce IL-12(interleukin 12) of human and mouse origin with high activity, the expression vector including above mutant gene and the use of them to DNA vaccine adjuvant. Particularly, it relates to IL-12p40 mutant gene which inhibits the secretion of IL-12p40 but normally secretes active IL-12p70 by making mutation at Asn-222 (human) or Asn-220(mouse) amino acid of IL-12p40, which acts as a competitive inhibitor of active form of IL-12, IL-12p70. Therefore, the IL-12p40 mutant gene of the present invention can be useful for DNA vaccination and gene therapy against various diseases, for example, AIDS, hepatitis C or hepatitis B, cancer, influenza, tuberculosis and malaria, which essentially require cellular immune responses for their therapy.

19 Claims, 11 Drawing Sheets

FIG. 1

```
Mouse  1    MCPQKLTISWFAIVLLVSPLMAMWELEKDVYVVEVDWTPDAPGETVNLTC    50

Human  1    MCHQQLVISWFSLVFLASPLVAIWELKKDVYVVELDWYPDAPGENVVLTC    50

Mouse  51   DTPEEDDITWTSDQRHGVIGSGKTLTITVKEFLDAGQYTCHKGGETLSHS   100

Human  51   DTPEEDGITWTLDQSSEVLGSGKTLTIQVKEFGDAGQYTCHKGGEVLSHS   100

Mouse 101   LLLLHKKENGIWSTEILKN    FKNKTFLKCEAPNYSGRFTCSWLVQRNM   147

Human 101   LLLLHKKEDGIWSTDILKDQKEPKNKTFLRCEAKNYSGRFTCWWLTTIST   150

Mouse 148   DLKFNIKSSSSPPDSRAVTCGMASLSAEKVTLDQRDYEKYSVSCQEDVTC   197

Human 151   DLTFSVKSSRGSSDPQGVTCGAATLSAERVRGDNKEYE YSVECQEDSAC   199

220
Mouse 198   PTAEETLPIELALEARQQNKYENYSTSFFIRDIIKPDPPKNLQMKPLKN   247

Human 200   PAAEESLPIEVMVDAVHKLKYENYTSSFFIRDIIKPDPPKNLQLKPLKNS   249
                                        222

Mouse 248   QVEVSWEYPDSWSTPHSYFSLKFFVRIQRKKEKMKETEEGCNQKGAFLV    296

Human 250   RQVEVSWEYPDTWSTPHSYFSLTFCVQVQGKSKREK       KDRVF T   291

Mouse 297   EKTSTEVQC KGGNVCVQAQDRYYNSSCSKWACVPCRVRS              335

Human 292   DKTSATVICRKNASISVRAQDRYYSSSWSEWASVPC     S           328
```

GENES OF IL-12P40 SUBUNIT MUTATED FOR IMPROVING THE ACTIVITY OF IL-12 AND USE THEREOF FOR DNA VACCINE ADJUVANT

CONTINUING DATA

This application is a national stage application of PCT/KR01/00408, filed Mar. 15, 2001 under 35 U.S.C. § 371.

FIELD OF THE INVENTION

The present invention relates to mutant IL-12p40 subunit genes producing highly active human and mouse Interleukin 12(IL-12), expression vector which contains those mutant genes and methods to use thereof for DNA vaccine adjuvant. Particularly, this invention relates to mutant IL-12p40 subunit genes which can secrete immunoactive IL-12p70 normally but reduce secretion of IL-12p40 by inducing mutation for amino acids Asn-222(mouse) or Asn-220(human) of IL-12p40 working as a competitive inhibitor to active IL-12.

BACKGROUND OF THE INVENTION

IL-12 is secreted by antigen presenting cells (APC) such as macrophages, monocytes and B cells after getting appropriate stimulation, and works as a regulator for many kinds of immune response in vivo. Particularly, IL-12 has a broad range of activities including proliferation of activated type 1 helper T (Th1) and natural killer (NK) cells, regulation of the production of many cytokines, induction of type 1 T helper cell immune responses, differentiation of CD8+ T cells, stimulation of hematopoietic stem cells (Hsieh, C. S. et al., *Science,* 260:547-549, 1993), and especially, regulation of immune response by promoting lytic activity of cytotoxic T lymphocytes (CTL) and NK cells (Robertson, M. J. and J. Ritz., *Oncologist,* 1:88-97, 1999; Trinchieri, G., *Annu. Rev. Immunol.,* 13:251-276, 1995). According to recent reports, peripheral blood mononuclear cells (PBMC) from human immunodeficiency virus (HIV)-infected patients produced five-fold less biologically active IL-12 (Chehimi, J. et al., *J. Exp. Med.,* 179:1361-1366, 1994), and mycobacterial and salmonella infections were found to lack of IL-12 receptor expression (de Jong, R. et al., *Science,* 280:1435-1438). Due to these roles of IL-12, it could induce strong immune response in vivo against virus, bacteria and various cancers. Therefore, the present inventors can expect development of many treatment agents using the present invention.

On the basis of the theory that IL-12 is related to the growth of memory Th1 and memory CTL cells (Stobie, L. et al., *Proc. Natl. Acad. Sci.* USA, 97:8427-8432, 2000; Mortarini, R. et al., *Cancer Res.,* 60:3559-3568, 2000; Mbawuike, I. N. et al., *J. Infect. Dis.,* 180:1477-1486, 1999), IL-12 is believed to be used as a effective vaccine adjuvant or a treatment agent against various diseases requiring cellular immune response. Considering metastasis or recurrence, which is the most difficult part of the cancer treatment, the inducing of memory immune response is especially necessary. However, as of today the exact mechanism of IL-12, which is connected to those effects, has not been cleared. But, based on current available data, these are some clues to the mechanism by which IL-12 sustains CD4+ Th1 cells. In the course of Th1 differentiation, production of IFN-γ is enhanced and IL-2 is diminished. Because IL-2 is a potent growth factor and IFN-γ is antiproliferative, IL-12 could function to sustain cell growth and viability or to prevent apoptosis of CD4+ IFN-γ T cells (Fuss, I. J. et al., *Gastroenterology,* 117:1078-1088, 1999; Marth, T. et al., *J. Immunol.,* 162:7233-7240, 1999). Also, IFN-γ which is increased by IL-12 augments expression of IL-15 (Zhang, X. et al., *Immunity,* 8:591-599, 1998), which is related to memory CD8+ T cell. Based on those reports, IL-12 is very useful in vaccine immunization since IL-12 is related not only to the early immune response but also to the memory immune response.

The biologically functional form of IL-12 is a 70 kDa heterodimer, IL-12p70, which consists of disulfide-bonded p40 and p35 subunits. The p40 subunit shares amino aid sequence homology with the IL-6 receptor, thus it belongs to the cytokine receptor superfamily, whereas p35 subunit has a distant but a significant relationship to the IL-6/granulocyte colony stimulating factor cytokine family (Gearing, D. P., and Cosman, D., *Cell,* 66:9-10, 1991).

The IL-12p40 is secreted as both a monomer and a homodimer in large excess over IL-12p70 both in vitro (D'Andrea et al., *J. Exp. Med.,* 176:1387-1398, 1992; Podlasky, F. J. et al., *Arch. Biochem. Biophys.,* 294:230-237, 1992) and in vivo (Mattner, F. et al., *Eur. J. Immunol.,* 23:2202-2208, 1993; Heinzel, F. P. et al., *Infect. Immun.,* 62:4244-4249, 1994). It has been demonstrated that IL-12p40 strongly antagonizes IL-12p70-mediated responses by binding competitively to IL-12 recepor in vitro (Gillessen, S. et al., *Eur. J. Immunol.,* 25:200-206, 1995; Ling, P. et al., *J. Immunol.,* 154:116-127, 1995), suggesting the critical role of IL-12p40 as a natural antagonist of IL-12p70. This is supported by several observations including a reduction in Th1 responses in IL-12p40 transgenic mice (Yoshimoto, T. et al., *J. Immunol.,* 160:588-594, 1998), the prevention of allogenic rejection in transplanted myoblasts engineered to produce IL-12p40 (Kato, K. et al., *Proc. Natl. Acad. Sci., USA,* 93:9085-9089, 1996), and the inhibition of tumor suppression activity of IL-12p70 by adenovirus expressing IL-12p40 (Chen, L. et al., *J. Immunol.,* 159:351-359, 1997). In contrast, there is a report describing a positive role of IL-12p40 in IL-12p70-mediated responses resulting in alloantigen-specific Th1 development under certain condition (Piccotti, J. R. et al., *J. Immunol.,* 157: 1951-1957, 1996). Furthermore, a novel function of IL-12p40 as a chemotactic molecule for macrophage was known by this inventors (Ha, S. J. et al., *J. Immunol.,* 163:2902-2908, 1999).

Various in vivo systems have been established in order to prove the anti-cancer effect of IL-12p70. However, there is a significant side-effect which could result in death if human recombinant IL-12p70 protein is directly injected into a cancer patient (Robertson, M. J. and Ritz, J., *Oncologist,* 1:88-97, 1996; Cohen, J., *Science,* 270:908, 1995). To prevent this side-effect and to be effective in economy, lots of studies have been conducted on gene therapy by using IL-12 gene, which now proves that IL-12 gene treatment is very effective and has no harm (Rakhmilevich, A. L. et al., *Proc. Natl. Acad. Sci.* USA, 93:6291-6296, 1996; Tahara, H. et al., *J. Immunol.,* 154:6466-6474, 1995; Lotze, M. T. et al., *Ann. N.Y. Acad. Sci.,* 795:440-454, 1996).

IL-12p70, a biologically active form of IL-12, is essential (Gulber, U. et al., *Proc. Natl. Acad. Sci.* USA, 88:4143-4147) for the gene-therapy using IL-12 and, cDNAs of p35 and p40 should be expressed in a cell at the same time. Many methods have been used to simultaneously express p35 and p40 subunit together in one cell. One of them is to use expression cassette through which p35 and p40 are placed in consecutive row and expressed each by each (Rakhmilevich, A. L. et al., *Proc. Natl. Acad. Sci.* USA, 93:6291-6296, 1996). Another one is to use internal ribosomal entry site (IRES) of encephalomyocarditis virus (EMCV) for simultaneous expression of both genes. These methods were successful in expressing IL-12p70 in one cell, but as mentioned above, not successful in removing the possibility that continuously expressed excessive IL-12p40 inhibits the biological action of IL-12p70.

To overcome this intrinsic defect, the genetic linkage of p35 subunit followed by p40 subunit was recently proposed by means of a DNA sequence encoding a protein linker commonly used in antibody engineering (Lieschke, G. J. et al., *Nat. Biotechnol.*, 15:35-40, 1997; Lode, H. N. et al., *Proc. Natl. Acad. Sci.* USA, 95:2475-2480, 1998; Lee, Y. L. et al., *Human Gene Ther.*, 9:457-465, 1998). Antagonistic effect of excessive IL-12p40 against biological activity of IL-12p70 could be surmounted in the above method. However, it is still not good enough having a problem that the activity of IL-12p70 was 5-100 times more decreased since it's structure may be changed when p35 and p40 are linked together. For the effective treatment against cancer or other diseases with IL-12 gene, it is required to induce IL-12p70 still having the same activity and prevent the secretion of IL-12p40.

Glycosylation has been known to contribute protein folding, secretion, conformation, stability and biological activity. The p35 and p40 subunits of human IL-12 express 219 and 328 amino acids that contain 56 and 22 amino acids of hydrophobic signal sequences, respectively. The analysis of human IL-12 amino acid sequence reveals three and four putative N-glycosylation sites within p35 and p40 subunits, respectively (Podlasky, F. J. et al., *Arch. Biochem. Biophys.*, 294:230-237, 1992). Stern et al. reported that after treatment of human IL-12 with tri-fluoromethanesulfonic acid or glycosidase F, IL-12p35 and IL-12p40 were reduced in molecular weight (Podlasky, F. J. et al., *Arch. Biochem. Biophys.*, 294:230-237, 1992). This suggests that p35 and p40 subunits of human IL-12 are composed of carbohydrates. In the same report, it was also demonstrated that the digestion of IL-12p35 with neuramidase followed by endo-α-N-acetylgalactosamimidase reduced its molecular weight, whereas IL-12p40 was unaffected by such treatment. These experiments indicate that the glycosylation of IL-12p35 is contributed by O-linked oligosaccharides and that IL-12p40 has no O-linked carbohydrates. And, in the analysis of N-glycosylation at Asn-135 and Asn-222 amino acid residues, it was revealed that Asn-222 is the N-glycosylation site. However the exact N-glycosylation sites of human and mouse IL-12 and its effects on the synthesis, secretion and biological activity of IL-12 have not been defined.

On the other hand, the study using IL-12 gene has been accelerated since cell-mediated immune response is required rather than humoral immune response for the prevention and treatment of many viral or bacterial diseases along with suppression of cancer formation. Hepatitis C is the representative virus-mediated disease and once infected with HCV, more than 50% patients become chronic and finally lead to liver cirrhosis or liver cancer (Alter, H. J. et al., *N. Engl. J. Med.*, 321:1494-1500, 1989). As of today, only α-interferon is known as a treatment agent for hepatitis C, but the effect is not good enough (10-30%) (Weiland, E. et al. *J. Virol.*, 66:3677-3682, 1992). So, more effective vaccine or treatment agents against HCV are urgently required. According to the medical test reports including both human and chimpanzee, HCV is related to specific humoral immune response and cell-mediated immune response as well (Prince, A. M. et al., *J. Infect. Dis.*, 165:438-443, 1992), and E1 and E2, structural protein of HCV is reported as a major antigen to induce protective immunity (Choo, Q. L. et al., *Proc. Natl. Acad. Sci.* USA, 91:1294-1298, 1994). Once more, cell-mediated immune response including CTL is preferably needed to remove HCV compared to humoral immune response (Cooper, S. et al., *Immunity,* 10:439-449, 1999; Rinaldo, C. et al., *J. Virol.*, 69:5838-5842, 1995).

DNA immunization is the most recent method to induce cell-mediated immune response. DNA immunization is differentiated with the existing one using dead or detoxicated pathogen or certain parts of pathogen in the matter of inserting DNA coding a specific component of pathogen directly to the human body. DNA immunization is also known to induce strong immune response against various infectious virus such as influenza, hepatitis B and human immunodeficiency virus (Ulmer, J. B. et al., *Science,* 259: 1745-1749, 1993; Michel, M. L. et al., *Proc. Natl. Acad. Sci.* USA, 92:5307-5311, 1995; Irwin, M. J. et al., *J. Virol.*, 68:5306-5044, 1994). In addition, DNA immunization is also reported to induce special immune response against capsid and E2 protein of HCV (Major, M. E. et al., *J. Virol.*, 69:5798-5805, 1995; Tedeschi, V. et al., *Hepatology,* 25:459-462, 1997).

However, DNA immunization is limited in use because expression frequency of an antigen is low in vivo. Some kind of costimulatory molecule genes which are necessary for the activation of immune cells were used to increase the effect of DNA immunization (Geissler, M. et al., *J. Immunol.,* 159:5107-5113, 1997; Iwasaki, A. et al., *J. Immunol.,* 158:4591-4601, 1997; Lee, S. W. et al., *J. Virol.*, 72:8430-8436, 1997). IL-12 gene was also used to induce immune response against HCV effectively (Lasartte, J. J. et al., *J. Immunol.,* 162:270-277, 1999). Those, however, has given unsatisfactory results so far especially in the DNA immunization with human and primates (Boyer, J. et al., *Keystone Symposium on DNA Vaccines Apr.,* 12-17, 1998).

The present inventors worked hard to produce genes which can express active IL-12p70 through the control of glycosylation and can minimize the secretion of IL-12p40 decreasing immune activity by action of IL-12. As a result, the mutant gene was obtained through the mutation of Asn-222, glycosylation site of human IL-12p40 subunit and Asn-220, glycosylation site of mouse IL-12p40 subunit. The obtained mutant genes which increase the expression of active IL-12p70 and decrease the secretion of IL-12p40 was used in small animal model, mice, along with HCV E2 gene for DNA immunization. Through this trial, the best cell-mediated immune response was induced and even this immune response was continued long period. Thus, it is certain that the mutant gene of the present invention is very useful as an adjuvant for DNA vaccine.

SUMMARY OF THE INVENTION

It is an object of this invention to provide mutant IL-12p40 gene which activates the basic role of IL-12 such as activation of CTL cells or enhancement of immune response through Th1 cells by mutating the glycosylation site which is essential in secretion of IL-12p40 in human or mouse, to decrease the secretion of IL-12p40 which inhibits the activation of IL-12p70 by binding the receptor of IL-12p70 competitively.

It is a further object of this invention to provide adjuvant which keeps and increases antigen-specific immune response by DNA immunization using expression vector containing the mutant IL-12p40 gene and DNA vaccine together.

BRIEF DESCRIPTION OF THE DRAWINGS

FIG. 1 shows the sequence homology of amino acids between human and mouse IL-12p40.

GI; Mouse which is immunized with 200 μg of pTV2.
GII; Mouse which is immunized with 100 μg of pTV2-HCV-gDsE2t and 100 μg of pTV2.
GIII; Mouse which is immunized with 100 μg of pTV2-HCV-gDsE2t and 100 μg of pTV2-mIL-12 wt.
GIV; Mouse which is immunized with 100 μg of pTV2-HCV-gDsE2t and 100 μg of pTV2-mIL-12mut.

Figure 5A:
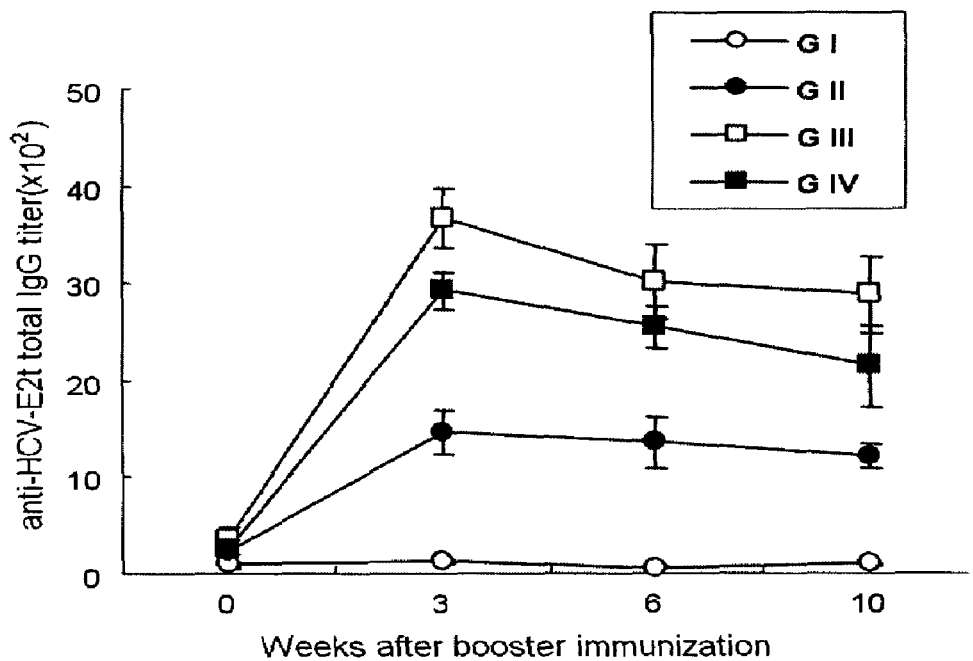
FIG. 5a shows a result measuring titer of total IgG antibody to HCV E2 in mouse serum which is immunized with DNA vector of the present invention.
Figure 5B:
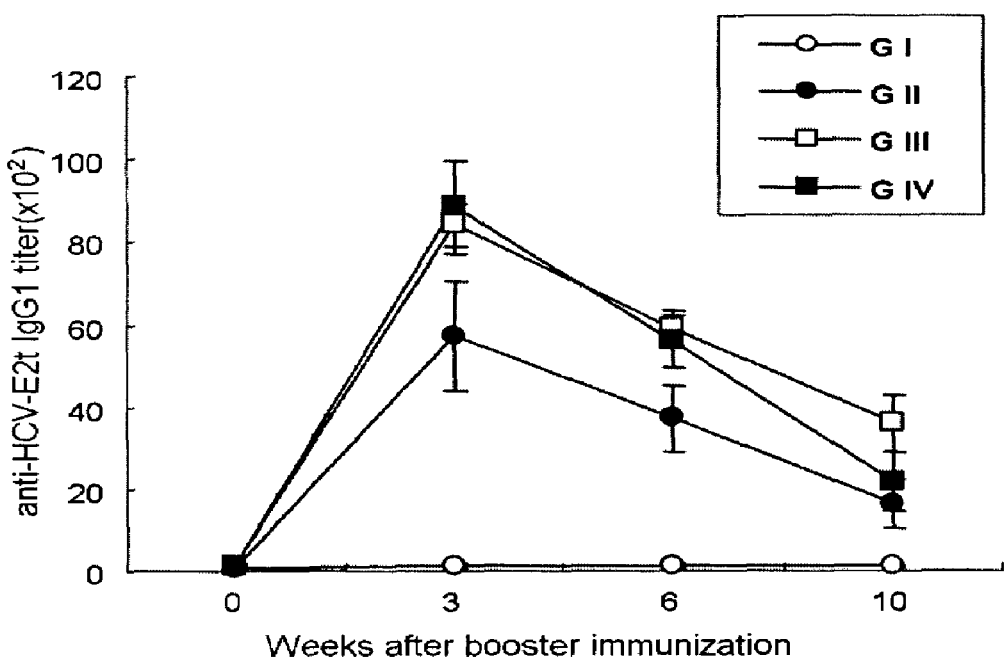

FIG. 5b shows a result measuring titer of IgG1 antibody to HCV E2 in mouse serum which is immunized with DNA vector of the present invention.

GI; Mouse which is immunized with 200 μg of pTV2.
GII; Mouse which is immunized with 100 μg of pTV2-HCV-gDsE2t and 100 μg of pTV2.
GIII; Mouse which is immunized with 100 μg of pTV2-HCV-gDsE2t and 100 μg of pTV2-mIL-12 wt.
GIV; Mouse which is immunized with 100 μg of pTV2-HCV-gDsE2t and 100 μg of pTV2-mIL-12mut.

Figure 5C:
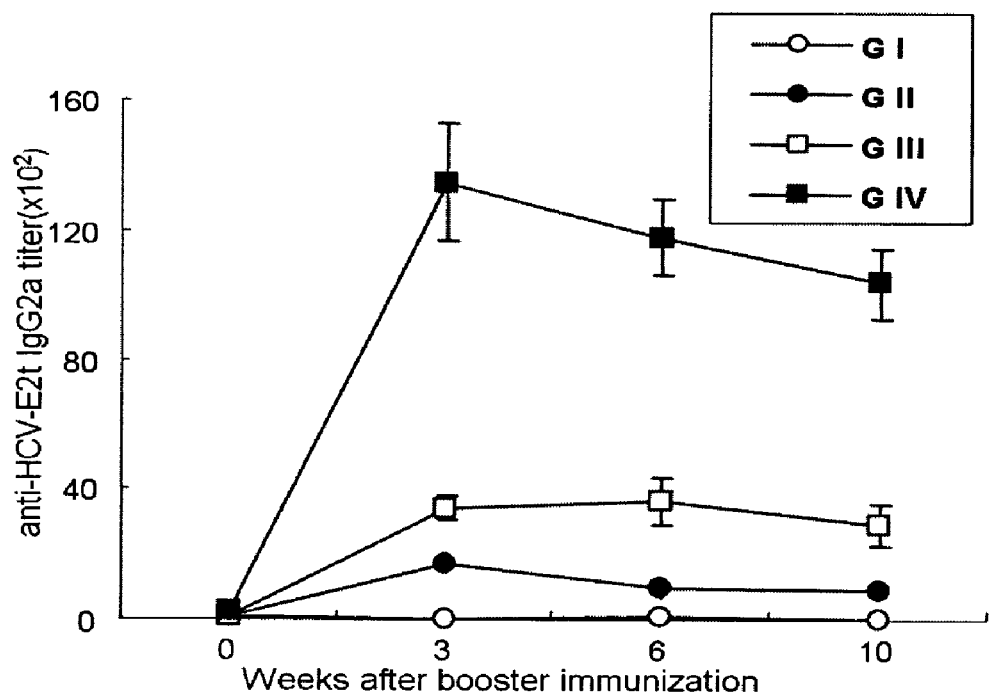

FIG. 5c shows a result measuring titer of IgG2a antibody to HCV E2 in mouse serum which is immunized with DNA vector of the present invention.

GI; Mouse which is immunized with 200 μg of pTV2.
GII; Mouse which is immunized with 100 μg of pTV2-HCV-gDsE2t and 100 μg of pTV2.
GIII; Mouse which is immunized with 100 μg of pTV2-HCV-gDsE2t and 100 μg of pTV2-mIL-12 wt.
GIV; Mouse which is immunized with 100 μg of pTV2-HCV-gDsE2t and 100 μg of pTV2-mIL-12mut.

Figure 5D:
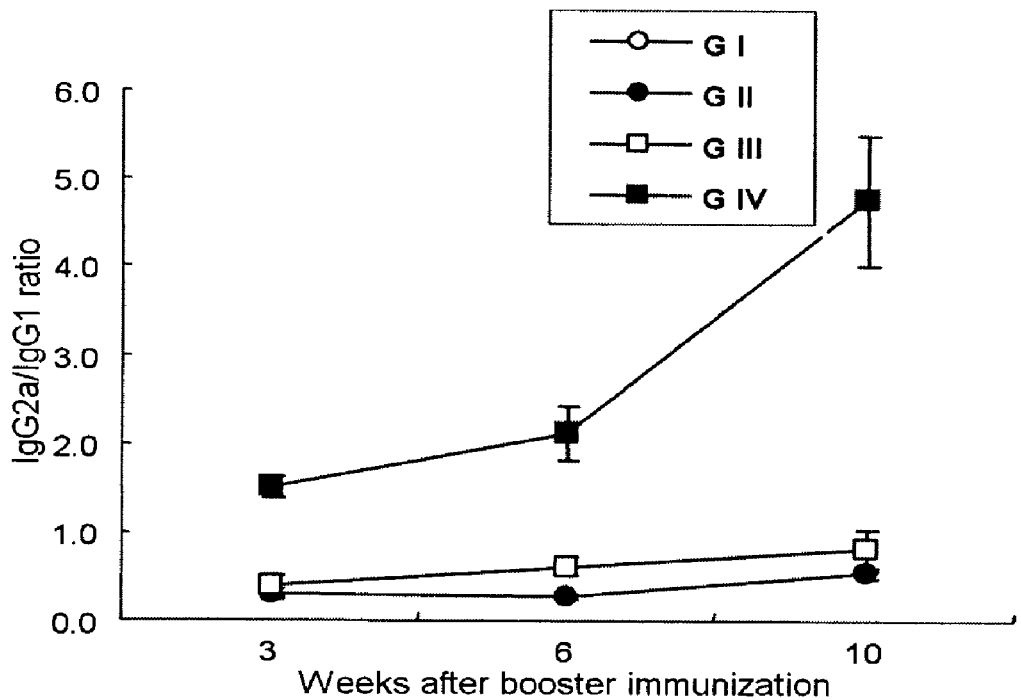

FIG. 5d shows a result measuring ratio of titer of IgG2a and IgG1 antibody (IgG2a/IgG1) to HCV E2 with mouse serum which is immunized with DNA vector of the present invention.

GI; Mouse which is immunized with 200 μg of pTV2.
GII; Mouse which is immunized with 100 μg of pTV2-HCV-gDsE2t and 100 μg of pTV2.
GIII; Mouse which is immunized with 100 μg of pTV2-HCV-gDsE2t and 100 μg of pTV2-mIL-12 wt.
GIV; Mouse which is immunized with 100 μg of pTV2-HCV-gDsE2t and 100 μg of pTV2-mIL-12mut.

FIG. 6a shows a result measuring IFN-γ production level from mouse splenocytes obtained 3 weeks after immunized with DNA vector of the present invention.

GI; Mouse which is immunized with 200 μg of pTV2.
GII; Mouse which is immunized with 100 μg of pTV2-HCV-gDsE2t and 100 μg of pTV2.
GIII; Mouse which is immunized with 100 μg of pTV2-HCV-gDsE2t and 100 μg of pTV2-mIL-12 wt.
GIV; Mouse which is immunized with 100 μg of pTV2-HCV-gDsE2t and 100 μg of pTV2-mIL-12mut.

FIG. 6b shows a result measuring IFN-γ production level from mouse splenocytes obtained 6 weeks after immunized with DNA vector of the present invention.

GI; Mouse which is immunized with 200 μg of pTV2.
GII; Mouse which is immunized with 100 μg of pTV2-HCV-gDsE2t and 100 μg of pTV2.
GIII; Mouse which is immunized with 100 μg of pTV2-HCV-gDsE2t and 100 μg of pTV2-mIL-12 wt.
GIV; Mouse which is immunized with 100 μg of pTV2-HCV-gDsE2t and 100 μg of pTV2-mIL-12mut.

FIG. 6c shows a result measuring IFN-γ production level from mouse splenocytes obtained 10 weeks after immunized with DNA vector of the present invention.

GI; Mouse which is immunized with 200 μg of pTV2.
GII; Mouse which is immunized with 100 μg of pTV2-HCV-gDsE2t and 100 μg of pTV2.
GIII; Mouse which is immunized with 100 μg of pTV2-HCV-gDsE2t and 100 μg of pTV2-mIL-12 wt.
GIV; Mouse which is immunized with 100 μg of pTV2-HCV-gDsE2t and 100 μg of pTV2-mIL-12mut.

Figure 7:
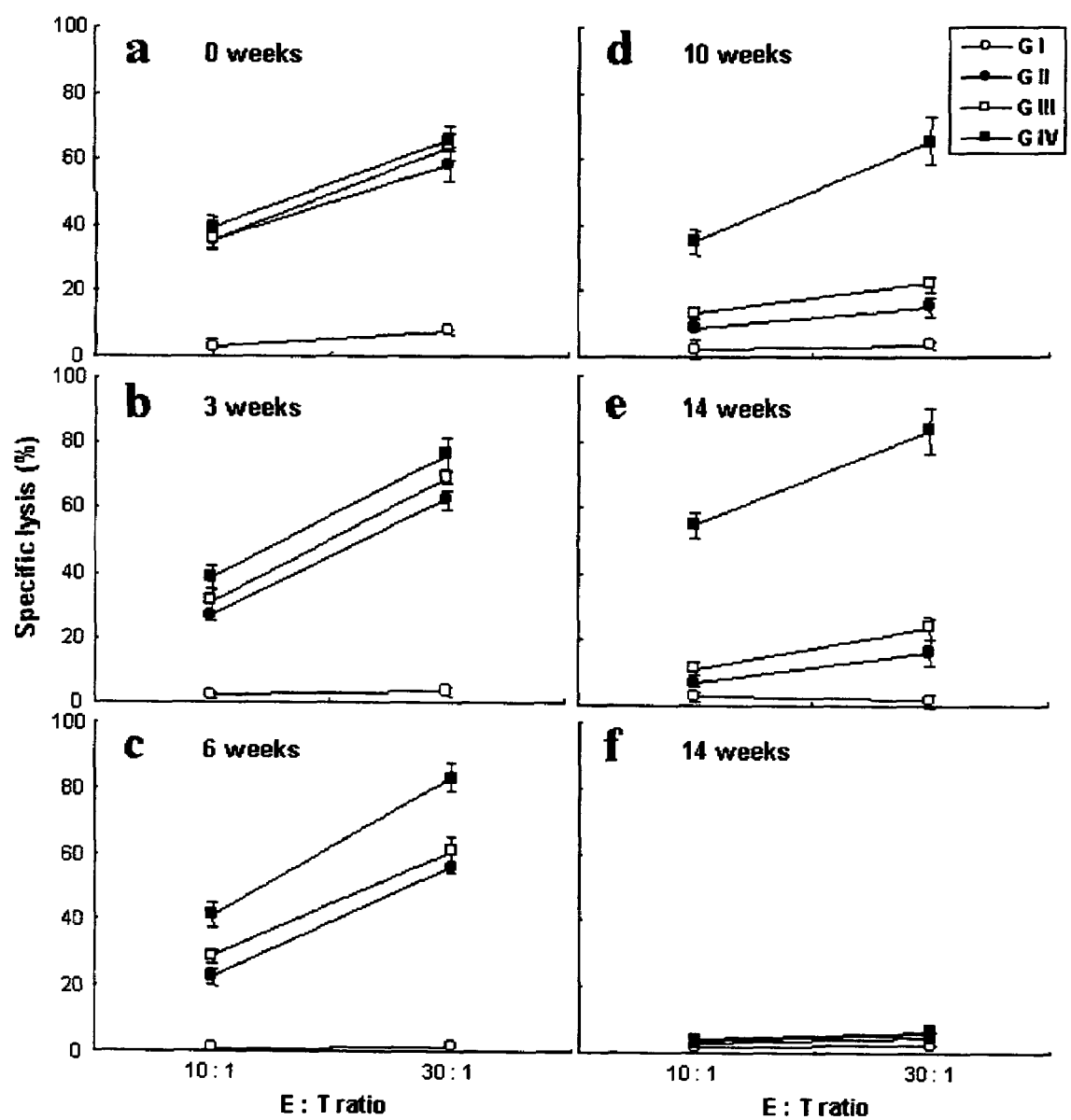

FIG. 7 shows a result measuring specific CTL activity to HCV E2 using engineered CT26 tumor cells expressing hghE2t after immunization with DNA vector of the present invention.

GI; Mouse which is immunized with 200 μg of pTV2.
GII; Mouse which is immunized with 100 μg of pTV2-HCV-gDsE2t and 100 μg of pTV2.
GIII; Mouse which is immunized with 100 μg of pTV2-HCV-gDsE2t and 100 μg of pTV2-mIL-12 wt.
GIV; Mouse which is immunized with 100 μg of pTV2-HCV-gDsE2t and 100 μg of pTV2-mIL-12mut.

a; right after immunization, b; 3 weeks after immunization,
c; 6 weeks after immunization, d; 10 weeks after immunization,
e; 14 weeks after immunization, f; 14 weeks after immunization, control (CT26-neo cells)

Figure 8A:
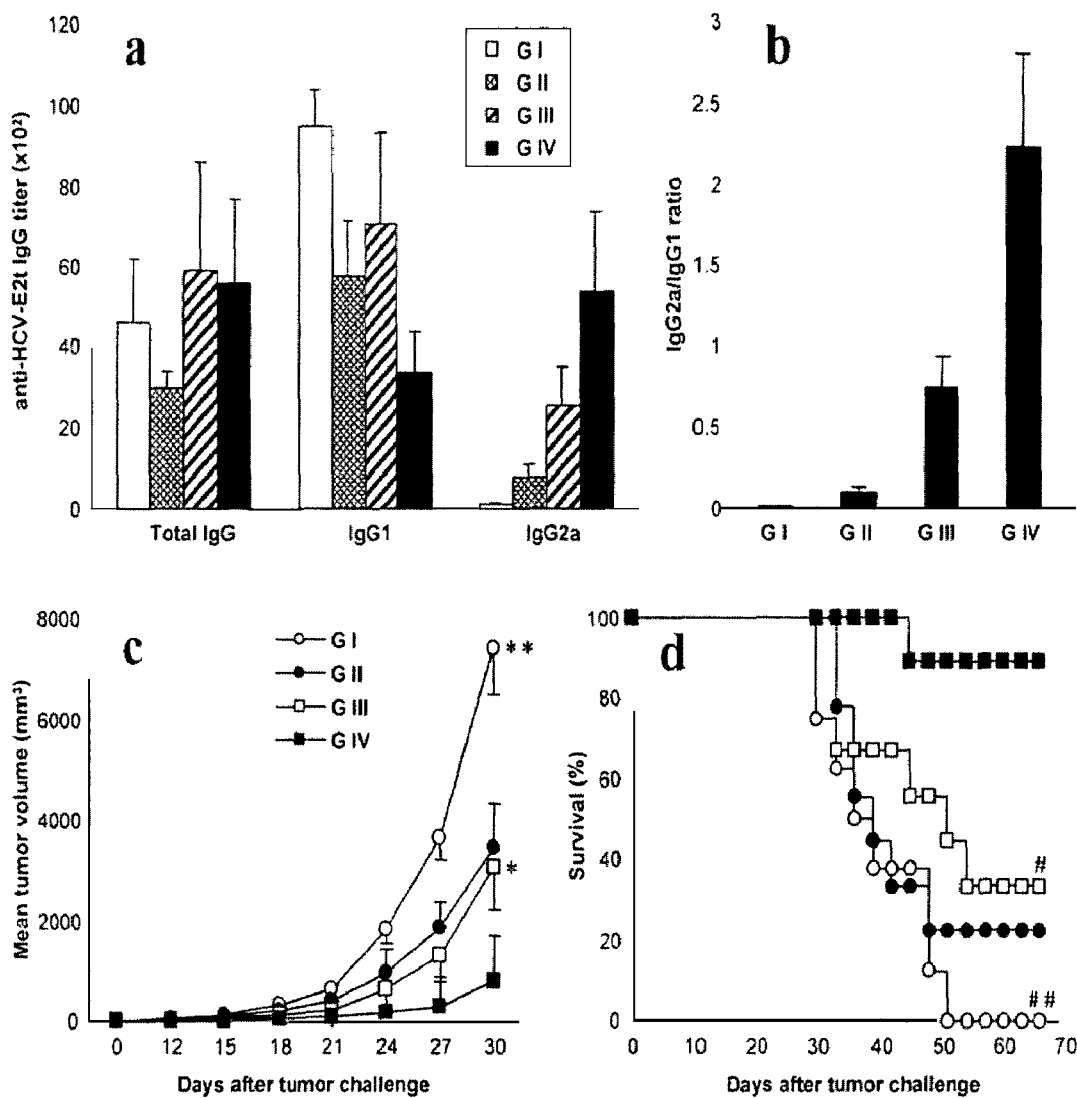

FIG. 8a shows a result measuring levels of total IgG, IgG1 and IgG2a to HCV E2 in mouse serum 2 weeks after challenge with engineered CT26 tumor cells expressing hghE2t into mice immunized with DNA vector of the present invention.

GI; Mouse which is immunized with 200 μg of pTV2.
GII; Mouse which is immunized with 100 μl of pTV2-HCV-gDsE2t and 100 μg of pTV2.
GIII; Mouse which is immunized with 100 μg of pTV2-HCV-gDsE2t and 100 μl of pTV2-mIL-12 wt.
GIV; Mouse which is immunized with 100 μg of pTV2-HCV-gDsE2t and 100 μg of pTV2-mIL-12mut.

FIG. 8b shows a result measuring ratio of titers of IgG2a and IgG1(IgG2a/IgG1) to HCV E2 in mouse serum 2 weeks after challenge with engineered CT26 tumor cells expressing hghE2t into mice immunized with DNA vector of the present invention.

GI; Mouse which is immunized with 200 μg of pTV2.
GII; Mouse which is immunized with 100 μg of pTV2-HCV-gDsE2t and 100 μg of pTV2.
GIII; Mouse which is immunized with 100 μg of pTV2-HCV-gDsE2t and 100 μg of pTV2-mIL-12 wt.
GIV; Mouse which is immunized with 100 μg of pTV2-HCV-gDsE2t and 100 μg of pTV2-mIL-12mut.

FIG. 8c shows a result measuring change of the IFN-γ production level of tumor cells expressing hghE2t into mice immunized with DNA vector of the present invention.

GI; Mouse which is immunized with 200 μg of pTV2.
GII; Mouse which is immunized with 100 μg of pTV2-HCV-gDsE2t and 100 μg of pTV2.
GIII; Mouse which is immunized with 100 μg of pTV2-HCV-gDsE2t and 100 μg of pTV2-mIL-12 wt.
GIV; Mouse which is immunized with 100 μg of pTV2-HCV-gDsE2t and 100 μg of pTV2-mIL-12mut.

FIG. 8d shows a result measuring survival rate of mice challenged with engineered CT26 tumor cells expressing hghE2t after immunization with DNA vector of the present invention.

GI; Mouse which is immunized with 200 μg of pTV2.
GII; Mouse which is immunized with 100 μg of pTV2-HCV-gDsE2t and 100 μg of pTV2.
GIII; Mouse which is immunized with 100 μg of pTV2-HCV-gDsE2t and 100 μg of pTV2-mIL-12 wt.
GIV; Mouse which is immunized with 100 μg of pTV2-HCV-gDsE2t and 100 μg of pTV2-mIL-12mut.

Figure 9:
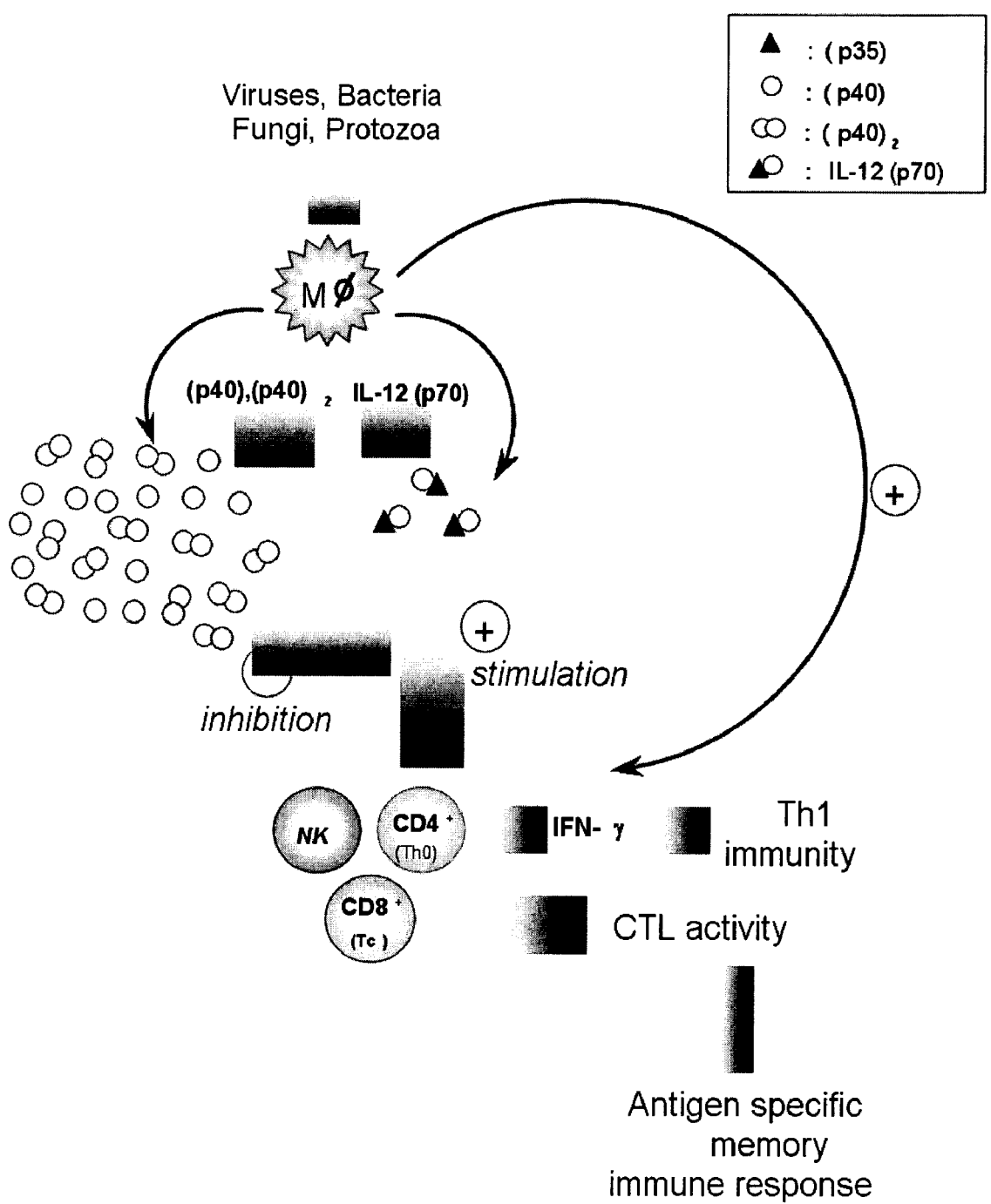

FIG. 9 shows a schematic view of biological function of IL-12 in vivo.

▲; p35,   ○; p40,
○ ○; (p40) 2,   ▲ ○; IL (p70)

DETAILED DESCRIPTION OF PREFERRED EMBODIMENTS

To achieve those objects, the present invention provides human or mouse mutant IL-12p40 subunit genes replaced Asn-222(human) or Asn-220(mouse) which is essential for the secretion of IL-12p40 with other amino acids.

The present invention provides gene construct and expression vector containing IRES sequence for co-expression of human or mouse genes of mutated IL-12p40 subunit and subunit itself.

And also, the present invention provides DNA vaccine vector containing and expressing HCV E2 gene, gene construct and expression vector containing p40 subunit gene which has mutated Asn-222(human) or Asn-220(mouse) sites.

Finally, the present invention provides a method for gene therapy or DNA vaccine immunization using this gene construct as an adjuvant for the enhancement of immune response.

Further features of the present invention will appear hereinafter.

Once again, the present invention is to provide human or mouse mutant IL-12p40 genes in which Asn-222(human) or Asn-220(mouse) playing a very important role in secretion of human IL-12p40 having SEQ. NO. 1 or mouse IL-12p40 having SEQ. NO. 2 are replaced with other amino acids.

Comparing with the amino acid sequence of human and mouse IL-12p40, Asn-220 of mouse IL-12p40 is located in the very similar context to Asn-222 of human IL-12p40 (FIG. 1).

More specifically, codon AAC designating Asn-222 of human IL-12p40 subunit can be changed with CUC, CAG or AUA etc, and amino acids coming under each of those are Leu, Gln and Ile. The present invention gives test examples demonstrating that AAC was changed into CTC or CAG on cDNA, and thus codon AAC was exchanged with CUC or CAG. Finally, the present invention provides mutant gene in which Asn-222 amino acid was replaced with Leu-222 (hp40-N222L) or Gln-222(hp40-N222Q).

Codon ACC designating Asn-220 of mouse IL-12p40 subunit which is compared with Asn-222 of human IL-12p40 subunit can be changed with CUC, CAG or AUA, and amino acids coming under each of those are Leu, Gln and Lle. The present invention provides mutant gene in which Asn-220 amino acid was replaced with Leu-220 (mp40-N220L) by changing AAC with CTC on cDNA.

The mutant genes, hp40-N222L, hp40-N222Q and mp40-N220L of the present invention are coding amino acid sequences noted as SEQ. NO. 3, SEQ. NO. 4 and SEQ. NO. 5 respectively.

The present invention provides gene construct containing IRES for simultaneous expression of subunit itself and human or mouse mutant IL-12p40 subunit gene, and expression vector including this gene construct.

First of all, the present invention provides hp40-N222L/IRES/hp35, hp35/IRES/hp40-N222L and mp35/IRES/mp40-N220L genes containing genes explained above. hp40-N222L/IRES/hp35 gene and hp35/IRES/hp40-N222L gene include gene encoding p35 subunit along with human p40 subunit having Leu-222 instead of Asn-222, while mp35/IRES/mp40-N220L gene includes gene encoding p35 subunit along with mouse p40 subunit whose Asn-220 sites were replaced with Leu-220. Both genes have IRES sequence for simultaneous expression of subunits. IRES from EMCV (encephalomyocarditis) is preferable for genes such as hp40-N222L/IRES/hp35, hp35/IREShp40-N222L and mp35/IRES/mp40-N220L, but not limited to thereof. IRES sequence is important in co-expression of genes coding p40 subunit and p35 subunit.

The present invention provides expression vectors, for example, pGX0-hp40-N222L/IRES/hp35 containing hp40-N222L/IRES/hp35, pGX0-hp35/IRES/hp40-N222L containing hp35/IRES/hp40-N222L and pTV2-mp35/IRES/mp40-N220L containing mp35/IRES/mp40-N220L as well.

The present invention shows an example in which pGX0 plasmid, a DNA vaccine vector becomes possible to be used in medical experiment by inserting kanamycin resistant gene instead of ampicillin resistant gene of pTV2 DNA vaccine vector (Song, M. K. et al., *J. Virol.*, 74:2920-2925, 2000), and hp40-N222L/IRES/hp35 gene and hp35/IRES/hp40-N222L gene were inserted in the part of that pGX0 plasmid which is ready for receiving foreign genes. And mp35/IRES/mp40-N220 gene was inserted into the foreign gene receiving part of pTV2 DNA vaccine vector. Besides the above plasmids used for making expression vectors, there are various vectors including for prokaryotes or eukaryotes, which makes possible to use a different vector for a different purpose. It is also possible to change the size and nucleotide sequence of gene which is to be inserted into the foreign gene receiving part of expression vector.

The expression vectors, pGX0-hp35/IRES/hp40-N222L and pGX0-hp40-N222L/IRES/hp35 of the present invention were deposited at Korean Collection for Type Cultures (KCTC), which is located at Korea Research Institute of Bioscience and Biotechnology (KRIBB), #52, Oun-dong, Yusong-ku, Taejon 305-333, Republic of Korea, on Feb. 26, 2001 (Accession No: KCTC 0969BP and KCTC 0970BP). And the pTV2-mp35/IRES/mp40-N220L was deposited at KCTC on Feb. 29, 2000 (Accession NO: KCTC 0745BP).

Figure 2:
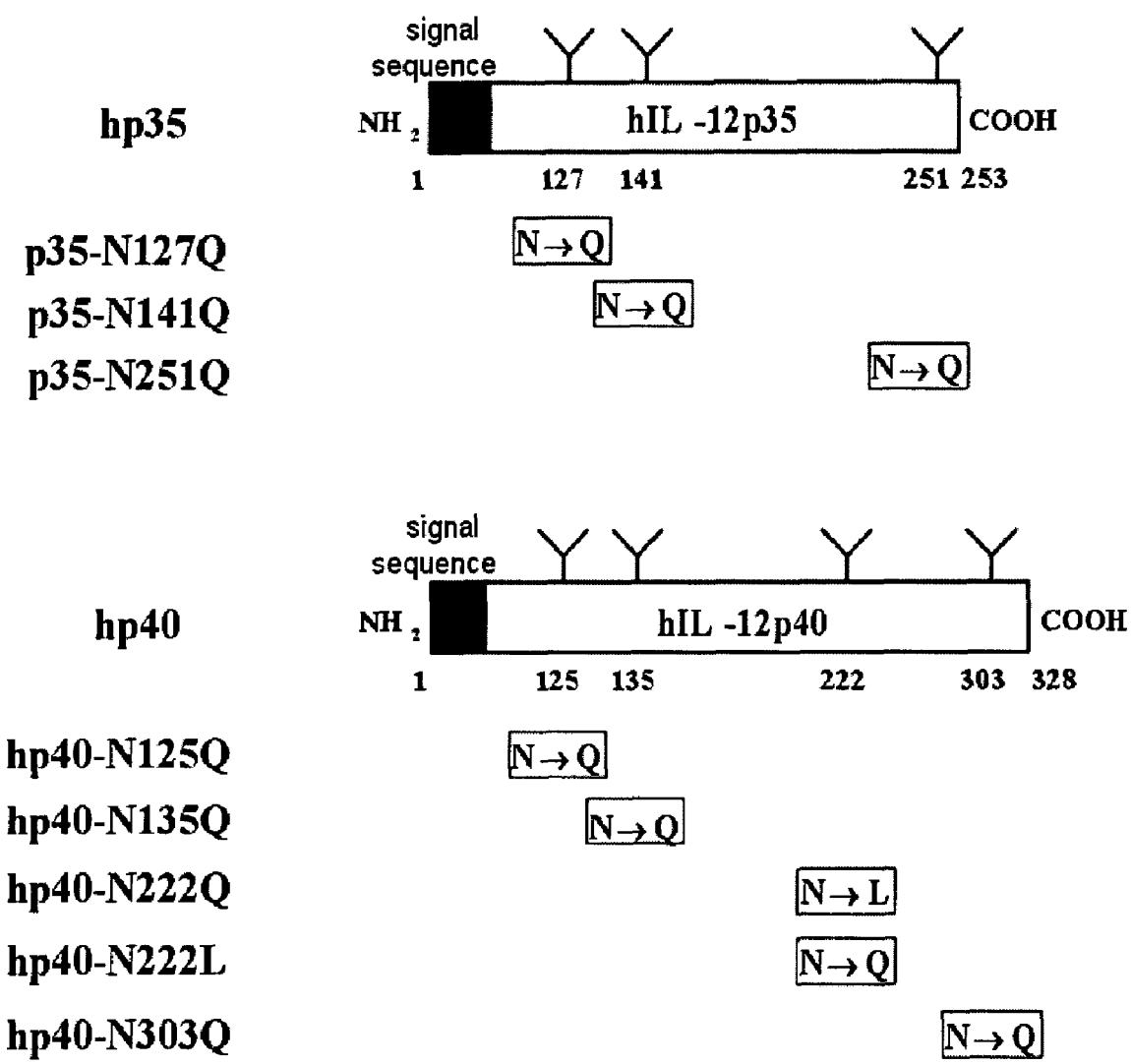
FIG. 2 shows p40 and p35 subunits of wild type human IL-12, and a amino acid changes at putative N-glycosylation sites of p40 and p35 subunits on the present invention.

Since the co-expression of p35 and p40 is essential to obtain a biologically active IL-12p70, bicistronic expression vectors, pGX0-hp40/IRES/hp35 and pGX0-hp35/IRES/hp40, were generated by using IRES of EMCV besides pCIN-hp35 or pCIN-hp40 expressing hp35 or hp40 respectively. To understand the influence of N-glycosylation on the synthesis, secretion and specific activity of human IL-12, Asn amino acid residue in putative N-glycosylation site existing on p35 and p40 subunit was replaced with other amino acid residues by site-directed mutagenesis (FIG. 2). Through the immunoblot of wild-type protein on mutant protein (FIGS. 3a, 3b and 3c), Asn-127, -141 of hp35 subunit and Asn-222, -303 of hp40 subunit were sure to be used for N-glycosylation.

To detect the effect of N-glycosylation of hp35 or hp40 on synthesis of heterodimerization and secretion of IL-12p70, cells were transfected with hIL-12 expression vector containing each wild-type gene or mutant gene, and then analyzed by ELISA using culture supernatant and cell lysate obtained therefrom.

As a result, it has been clarified that Asn-127 of hp35 causes decrease of heterodimerization and secretion of IL-12p70. However, compared with wild-type hp35, Asn-141 of hp35 seems relatively not to affect much to the heterodimerization and secretion of IL-12p70 and IL-12p40 (TABLE 1).

In addition, the mutation of Asn-135 or Asn-222 of hp40 subunit significantly decreases the secretion of IL-12p40, while does not affect the secretion of IL-12p70. Especially, the secretion of hp40 dropped to the degree of 8% relatively to the wild-type hp40 by Asn-222. Although Asn-135 of hp40 is not a N-glycosylation site, it still causes decrease of the secretion of hp40, which means Asn of Asn-135 itself plays an important role in the secretion of hp40. Even though amino acid of Asn-222 was replaced with Gln or Leu, the secretion of hp40 was still decreased, suggesting that was because of the loss of N-glycosylation at Asn-222 (TABLE 1). Thus, N-glycosylation at Asn-222 is required not for the secretion of heterodimer hIL-12, hIL-12p70 but for the secretion of hIL-12p40 only.

Considering all those results together, the present inventors verified that N-glycosylation at Asn-222 is necessary for the secretion of hIL-12p40, but not required for the secretion and heterodimerization of hIL-12p70, in the meantime N-glycosylation at Asn-127 of hp35 plays an important role in the secretion and heterodimerization of hIL-12p70.

To investigate the effect on biological activity of N-glycosylation of hIL-12, IFN-γ induction ability of wild-type hIL-12 and its derivatives containing putative N-glycosylation site mutation were analyzed by ELISA.

As a result, in the matter of IFN-γ induction ability, IFN-γ induction ability in culture supernatant obtained by co-transfection with wild-type hp35 and hp40 mutants in which Asn-135 and/or Asn-222 were mutated was increased in comparison with that of wild-type or other hp40 mutants (TABLE 1). And, when hp40 was supplied in the culture supernatant, the increased IFN-γ induction ability had come down to the similar level with that of wild-type (TABLE 1). Thus, it is suggested that these results are attributed to the relatively low level of hIL-12p40, known as an antagonist against hIL-12p70, in culture supernatant of mutants containing hp40-N135Q and/or hp40-N222Q, and the activity of hp70 produced from mutation of Asn-135 and/or Asn-222 does not increased by the mutation itself.

Meanwhile, to examine the effect of glycosylation of hp40 at Asn-222 on the decrease of secretion of hIL-12p40, cells were co-transfected with expression vector containing certain amount of mutant gene and various amount of wild-type hp35 DNA, then cultured. Finally, the induced amount of IFN-γ was measured by ELISA.

Generally, p35 subunit is not secreted solely but secreted in the form of IL-12p70 binding to p40, while p40 subunit is secreted in the form of monomer or homodimer, which suggests that not p35 but p40 subunit is a major fact inducing secretion of IL-12p70. Corresponding to this, the amount of hIL-12p70 secretion was increased in proportion to the amount of transfected hp35 DNA in both wild-type hp40 and hp40-N222Q mutant (TABLE 1). That means once hp40 having secretion defect is bound with hp35 subunit, it can be secreted in the form of IL-12p70, and thus, hp35 subunit seems to perform its another function in secretion of hIL-12p70. According to a recent report, the conformational change of hp40 is due to the binding with hp35 (Yoon, C. et al., EMBO J., 19:3530-3534, 2000), which also suggests that hp35 subunit can contribute to the secretion of IL-12p70. Conclusively, hp40 including glycosylation at Asn-222 itself has a defect in secretion but once it is bound with hp35, hp40 may be conformationally changed in its form and its conformational change could expose or generate the covered or new secretion signal, respectively, and then induce the secretion of heterodimer.

To decrease the secretion of p40 by inducing co-expression of p35 and p40 in a cell, and to decrease the amount of p40 secretion by inducing formation of p40 in which p40 gene is located behind IRES because the degree of gene expression using IRES is rather lower than using cytomegalovirus (CMV) promoter, hp40/IRES/hp35 and hp35/IRES/hp40 vectors were constructed. And also, hp40-N222L/IRES/hp35 and hp40/IRES/hp40-N222L in which hp40 gene had been replaced with hp40-N222L gene in each plasmid were generated (TABLE 1). Compared hp40/IRES/hp35 with hp40-N222L/IRES/hp35, hp40 was less secreted to the degree of 5% in the later. On the other hand, when hp35 and hp40-N222L were electroporated, hp40 was secreted to the degree of 8%. When hp35 and hp40-N222L were electroporated, it is possible for the two plasmids not to be transfected both of them into a cell. Besides, as hp40-N222L gene is expressed alone in a cell, the small amount of hp40 is secreted without the secretion of hp70. Therefore hp40 is supposed to be secreted more in hp40-N222L plus hp35 than in hp40-N222L/IRES/hp35 in which hp35 and hp40-N222L genes are expressed at the same time. Comparing hp40/IRES/hp35 with hp35/IRES/hp40, the secretion and expression of hp70 were not much different, but the secretion and expression of hp40 were significantly decreased in hp35/IRES/hp40 since the expression of hp40 was depressed by locating hp40 gene behind IRES. In the case of hp35/IRES/hp40-N222L made by inserting hp40-N222L gene instead of hp40 gene, the secretion level of hp40 dropped to 0.3%. Thus, it is confirmed through the present experiment that hp35/IRES/hp40-N222L is the one that can keep the secretion level of hp70 and at the same time minimize the secretion of hp40.

In addition, the present invention provides DNA vaccine vector, containing and expressing E2 gene of HCV-1b, and gene construct having p40 subunit gene which is mutated at Asn-222(human) or Asn-220(mouse).

To inspect the possibility for the use of hIL-12 mutant gene of the present invention in gene therapy as a DNA vaccine, the sequence of mouse IL-12p40(mp40) gene homologous to Asn-222 of hp40 gene was searched. Asn-220 of mp40 was located in the very similar context to that of Asn-222 of hp40, but this amino acid was not known to be N-glycosylated until now (FIG. 1). Therefore, the present inventors generated pCIN-mp40-N220L vector containing the mutant mp40 gene, mp40-N220L, in which amino acid of Asn-220 was replaced with Leu by site-directed mutagenesis.

To generate a vector encoding mouse p35 and p40 subunits and being used for the DNA immunization, pTV2-mp35/IRES/mp40 vector was constructed by inserting mp35/IRES/mp40 fragment into pTV2 vector, an eukaryotic expression vector used as a DNA vaccine vector in small animals (Lee et al., *J. Virol.*, 72:8430-8436, 1998; Cho et al., *Vaccine*, 17:1136-1144, 1999). And, the pTV2-mp35/IRES/mp40-N220L vector, containing Asn-220 mutant gene of mouse IL-12p40 and expressing p35, was constructed based on the observation that hp35/IRES/hp40-N222L gene can sustain the secretion of hp70 while can minimize the secretion of hp40.

Figure 4:
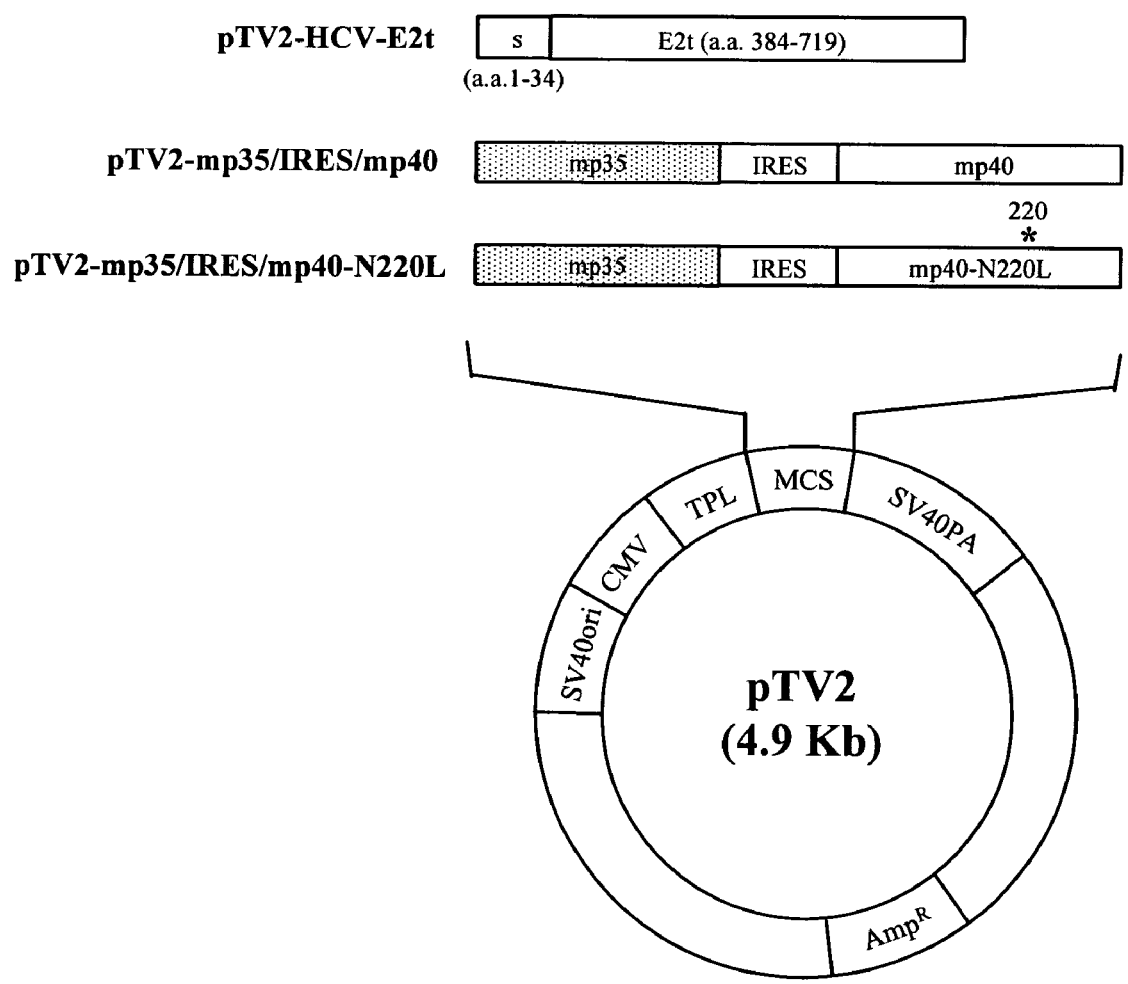
FIG. 4 shows a expression vector of the present invention which is inserted with envelope glycoprotein 2(E2) gene of hepatitis C virus (HCV) and wild-type or mutant mouse IL-12 gene.

The pTV2-mp35/IRES/mp40-N220L vector of the present invention was deposited at Gene Bank of Korea Research Institute of Bioscience and Biotechnology on Feb. 29, 2000 (Accession No: KCTC 0745BP).

pTV2-HCV-E2 DNA vaccine vector which can express HCV-E2 protein in eukaryotic cells was constructed (Song M. K., et al., *J. Virol.*, 74:2920-2925, 2000). As seen in FIG. 4, pTV2-HCV-E2 DNA vaccine vector is consist of simian virus 40 replication origin (SV40 ori), cytomegalovirus (CMV) promoter, tripartite leader sequence (TPL) of adenovirus, multiple cloning sequence (MCS), SV40 polyadenylation sequence (poly A) and ampicillin resistance gene (AmpR). And also, HCV-E2 gene is cloned in MCS of this vector. Carboxyl-terminal (C-terminal) containing hydrophobic amino acid residue of E2 gene used in the present invention was removed to facilitate protein secretion. And to help protein expression and cell secretion, aminocyl-terminal (N-terminal) and signal sequence(s) of herpesvirus (HSV) glycoprotein D (gD) were linked.

To analyze the effect of Asn-220 mutation of mouse IL-12p40 on the secretion of IL-12p40 or IL-12p70, the secretion level of mouse IL-12 was analyzed by ELISA with both culture supernatants and lysates of cells transfected with above vectors. As a result, mp40-N220L mutants showed similar characteristics to Asn-222 mutants of hp40 in the point of the secretion of IL-12p40 or IL-12p70 and its biological activity (TABLE 1).

Finally, the present invention provides a method for gene therapy or DNA vaccine immunization using this gene construct containing mutant p40 subunit gene whose Asn-222 (human) or Asn-220 (mouse) is mutated as an immune enhancer.

And this method can be useful for prevention and treatment against various diseases, for example, AIDS, hepatitis C or hepatitis B, cancer, influenza, tuberculosis and malaria, which essentially require cellular immune responses for their therapy.

In a previous report, DNA vaccination of plasmid encoding HCV E2 antigen (pTV2-gDsE2t) was sufficient to induce the antigen-specific and cell-mediated immune responses after 3 weeks post-immunization. To determine whether the mutant mIL-12 gene can affect the efficient antigen-specific immune response in vivo compared with wild-type mIL-12 gene, and to inspect whether the effect can be maintained for a long time, mice were immunized and boosted with the DNA vaccine vector of the present invention and production of HCV E2 specific antigen was analyzed by ELISA.

As a result, HCV E2 DNA vaccine induced systemic HCV E2-specific total IgG, IgG1 and IgG2a levels significantly higher than negative control values, and coinjection with mIL-12mut gene or mIL-12 wt gene showed the similar total IgG level compared to HCV E2 DNA vaccine only. However, the level of IgG1 was similar among the groups injected with HCV E2 DNA. In contrast, the level of IgG2a against HCV E2 slightly increased in mIL-12 wt group and significantly increased in mIL-12mut group compared with HCV E2 DNA immunized only group. In addition, the ratio of IgG2a/IgG1, which is generally accepted as an indirect indicator of Th1 immunity, was the highest in the mIL-12mut group, which showed the similar pattern of IgG2 level (FIGS. 5a, 5b, 5c and 5d). These data represent that mIL-12mut gene significantly affected the shift of IgG subclasses from IgG1 to IgG2a in humoral immune response compared to mIL-12 wt or HCV E2 only group, suggesting that IL-12mut may induce Th1 type immune response. And these effects maintained for 0, 3, 6, 10 weeks after booster immunization.

To investigate the effect of mIL-12mut gene on Th1 immune response, which is one of the parameter used to evaluate the potency of cell-mediated immune response, IFN-γ expression of splenocytes was analyzed.

As a result, HCV E2 DNA immunized group without cytokine gene showed the increased level of IFN-γ in proportion to the concentration of hghE2t protein, whereas mock plasmid immunized group did not. Expectedly, the level of IFN-γ induction in mIL-12 wt group was more enhanced than in HCV E2 only group and mIL-12mut group showed up to 2-3 times higher IFN-γ production than mIL-12 wt group (FIGS. 6a, 6b and 6c), suggesting that mIL-12p70 increases the antigen-specific Th1 immune response and mIL-12p40 inhibits the induction of Th1 immune response by IL-12p70 in vivo.

As noted above, mIL-12mut gene contributed to the long-term Th1 immune response in HCV E2 DNA immunization. To determine whether the long-term. Th1 immune response induction by the expression of mIL-12mut gene correlates with CTL immunity, the major cell-mediated immune response, and if so, to find out whether mIL-12mut gene can affect the maintenance of CTL activity in DNA immunization model, the present inventors performed the CTL assay with splenocytes of DNA immunized mice at various weeks after booster immunization.

As a result, two weeks after boost, all groups, except for mock plasmid immunized group, showed very strong antigen-specific CTL activity. However, there was little significant difference among HCV E2 only, mIL-12 wt and mIL-12mut groups. In mIL-12 wt coimmunized group, CTL response was more increased than in HCV E2 only group in overall period, indicating that mIL-12 gene played a role in the enhanced CTL generation. Interestingly, the difference in CTL activity between mIL-12mut group and the other two groups, HCV E2 only and mIL-12 wt group, was more and more extensive as the time after booster immunization is longer. Especially, at 10 weeks, CTL response was very low in HCV E2 only and mIL-12 wt groups, suggesting that the frequency of antigen-specific CTL significantly decreased after long period, whereas mIL-12mut group showed the CTL activity 5 to 10 times higher than the other two groups, sustaining the antigen-specific CTL response (FIG. 7). As a control, when CT26-neo cell was used as the target cell, no lysis was observed in all groups, suggesting that CTL activity observed in this experiment is HCV E2-specific.

And, the present inventors measured the frequency of HCV E2 specific CD8+ cells in vivo to confirm the effect of induction and maintenance of antigen-specific CD8+ T cell stimulated by mIL-12. Two types of immuno assay methods were used. First one is counting the number of antigen-specific IFN-γ producing cells. To investigate whether the enhancement of CTL activity is originated from the secretion of antigen-specific CD8+ T cell, CD8+ cells were isolated, and stained with PE conjugated anti-mouse IFN-γ antibody or control PE-conjugated isotype-matched antibody. Stained cells were analyzed by FACSCalibur flow cytometry (Becton Dickinson), and then induction of IFN-γ was observed. As a result, mice coimmunized with mIL-12mut gene had a 3 to 7-fold enhancement in the frequency of CD8+ IFN-γ producing cells compared with HCV E2 only and mIL-12 wt groups at 0, 3, 6, 10 or 14 weeks after booster immunization, which showed correlation with the result in CTL response. By contrast, in isotype-matched control experiment, there was no difference among all groups. Similarly to the result of CTL assay, the difference of IFN-γ producing CD8+ T cell frequency among immunization groups was not extensive at 2-3 weeks after booster immunization. These data demonstrate that the expression of mIL-12mut gene sustained the frequency of CD8+ IFN-γ producing T cells after DNA immunization for a long time.

To investigate the frequency of antigen-specific CD8+ T cells, the frequency of HCV E2 specific CD8+ T cells was measured by the other assay method, limiting dilution assay (LDA). Splenocytes of booster immunized mice were diluted with various concentration, and cultured with CT-26 cells expressing E2. And then, CTL activity of antigen-specific stimulated CD8+ T cell was measured. The result of limiting dilution assay was similar with that of intracellular staining assay. Namely, the highest frequency of antigen-specific CD8+ T cell was observed in mIL-12mut group even in early stage of immunization, and this frequency had been remained over 14 weeks after booster immunization (TABLE 2).

The frequency of HCV E2 specific CD8+ T cells without booster immunization was also observed according to the time. Overall frequency of antigen-specific CD8+ T cell was slightly decreased, but the highest frequency of antigen-specific CD8+ T cell was observed in mIL-12mut group (TABLE 2).

In this regard, it might be suggested that the role of IL-12p70 itself in cell-mediated immune response in vivo is to induce the activation of Th1 and CTL from the very beginning and to maintain it for a long time, whereas IL-12p40 inhibits the IL-12p70 as an antagonist in vivo.

To confirm the Th1 and CTL immunity induced by mIL-12mut gene in vivo, and to examine that the correlation of protective immunity with Th1 and CTL immune response, CT26-hghE2t tumor cells expressing hghE2t were injected in the groups of the immunized mice at 12 weeks after the booster immunization. 2 weeks after injection, relative levels of antigen-specific IgG, IgG1, IgG2 and the ratio of IgG2a/IgG1 were determined (FIG. 8a and FIG. 8b). As a result, highest level of IgG2a/IgG1 ratio was observed in mIL-12mut group, suggesting that Th1 immune response can be induced by mIL-12mut even in tumor injection.

Tumor size has been measured for 30 days. Particularly, the mean local tumor growth was determined by measuring the volume and diameter of tumors with calipers every three days. Also, the survival rates of these mice were determined by observing for about 70 days. The group of mice immunized with mIL-12mut induced strong Th1 immune response. The group of mIL-12 wt immunization displayed the delayed tumor growth in contrast to the group of only pTV2-gDsE2t immunization (FIG. 8c), whereas the group of mIL-12mut immunization showed the significantly delayed tumor growth. In control group, most of mice had tumor and died within 50 days, but 90% of mice in the group of mIL-12mut could survive after 70 days (FIG. 8d). Thus, these data suggest that HCV E2-specific Th1 and CTL responses induced by mIL-12mut gene of the present invention confers in vivo protection against the challenge of modified tumor cells expressing specific antigen.

The present inventors verified that human or mouse mutant Il-12p40 subunit containing mutant Asn-222 (human) or Asn-220 (mouse) which is essential for the secretion of IL-12p40 is very useful for DNA vaccine immunization and gene therapy as an adjuvant. Thus, the present invention provides an adjuvant containing human or mouse mutant IL-12p40 gene as an effective component for DNA immunization and gene therapy which can induce antigen-specific immune response for prevention and treatment against various diseases.

This adjuvant can induce immune response, if used with DNA vaccine, by increasing the secretion of IFN-γ from CD8+ or T helper cells and the hydrolysis activity of cytotoxic T lymphocytes (CTL).

EXAMPLES

Practical and presently preferred embodiments of the present invention are illustrative as shown in the following Examples.

However, it will be appreciated that those skilled in the art, on consideration of this disclosure, may make modifications and improvements within the spirit and scope of the present invention.

Example 1

Construction of Human IL-12 Expression Vectors

<1-1> Construction of Human IL-12 Expression Vectors

The cDNAs of human p35 (820 bp) and p40 (1050 bp) subunits were cloned and amplified using reverse transcriptase-polymerase chain reaction (RT-PCR, PCR System 2400, Perkin Elmer). The each amplified cDNA was subcloned into SmaI region of the universal vector, pSK (Stratagene, La Jolla, Calif.) and then pSK-hp35 and pSK-hp40 were constructed.

To generate a bicistronic vector encoding hp35 and hp40 genes, pSK-internal ribosomal entry site (IRES) vector was constructed. IRES gene of encephalomyocarditis virus (EMCV) obtained by RT-PCR was subcloned between SmaI and PstI sites of pSK plasmid pSK-IRES vector was cut by EcoRV, and added end of p40 DNA fragment obtained by treating pSK-hp40 with Xba I and BamH I was added to thereof using T4 DNA polymerase, then pSK-hp40/IRES was produced. And then pSK-hp40/IRES/hp35 plasmid in which p40, IRES, p35 genes are arranged in order, was constructed by the insertion of p35 DNA fragment from pSK-hp35 treated with Nco I and Sac I, to pSK-hp40/IRES.

pSK-hp35/IRES/hp40 was also constructed pSK-IRES vector was cut by EcoRV, and hp35 DNA fragment obtained from pSK-hp40/IRES/hp35 treated with Nco I and Not I was added to thereof. pSK-hp35/IRES/hp40 plasmid was completed by adding hp40 fragment obtained by cutting pSK-hp40 with Nco I and BamH I. hp40/IRES/hp35 and hp35/IRES/hp40 genes were cloned into Spe I/Not I and Xho I/Not I sites of pGX0 vector to create pGX0-hp40/IRES/hp35 and pGX0-hp35/IRES/hp40 expression vectors which can express active IL-12p70 in mammalian cells. pGX0 vector was constructed by inserting anticanamycin gene into pTV2 vector (Song, M. K. et al., *J. Virol.*, 74:2920-2925, 2000).

<1-2> Construction of p40 Subunit Expression Vector

To create p40 subunit expression vector, pCIN-hp40/IRES/hp35 vector was cut by SacII and Not I (to eliminate gene encoding p35 subunit), and self-ligated with T4 DNA polymerase, and then named as pCIN-hp40.

<1-3> Construction of p35 Subunit Expression Vector

To create p35 subunit expression vector, p35 DNA fragment was obtained from pCIN-hp40/IRES/hp35 vector by cutting and ligation with Nco I and T4 DNA polymerase. This p35 DNA fragment was inserted into XhoI and Not I restriction enzyme sites of pCI-neo vector, and then named as pCIN-hp35.

Example 2

Construction of Mouse IL-12 Expression Vectors

<2-1> Construction of Human IL-12 Expression Vectors

To generate a bicistronic vector encoding mouse p35 and p40 genes, pSK-IRES/mp40 vector was constructed by inserting p40 DNA fragment obtained from mouse IL-12p40 PCR product (Schoenhaunt, D. S. et al., *J. Immunol.*, 148: 3433-3440, 1999) treated with NcoI and BamH I into cleaved pSK-IRES vector containing IRES of EMCV. And pSK-mp35/IRES/mp40 plasmid was constructed by inserting mouse p35 DNA fragment into pSK-IRES/mp40 using BamH I and T4 DNA polymerase. Finally, pCIN-mp35/IRES/mp40 expression vector which can express active IL-12p70 in mammalian cells was generated by inserting mp35/IRES/mp40 gene into XhoI and NotI sites of pCI-neo vector (Promega).

<2-2> Construction of p40 Subunit Expression Vector

To create wild type mouse p40 subunit expression vector, p40 DNA fragment was obtained from pSK-mp35/IRES/mp40 vector treated with NcoI and SacI. pGEX-KG-mp40 was created by inserting this p40 DNA frgment into PGEX-KG vector (Clontech) treated with same restriction enzymes. pGEX-KG-mp40 was treated with EcoRI and NotI, and inserted into EcoRI and NotI sites of pCI-neo vector. So, pCIN-mp40 expression vector was generated.

<2-3> Construction of p35 Subunit Expression Vector

To create wild type mouse p35 subunit expression vector, p35 DNA fragment was obtained from pSK-mp35/IRES/mp40 vector treated with XhoI and EcoRI. pCIN-mp35 expression vector was constructed by inserting this DNA fragment into XhoI and EcoRI sites of pCI-neo vector treated with same restriction enzymes.

Example 3

Construction of IL-12p40 and IL-12p70 Which have Partially Mutated Glycosylation Seven Asn codons which are expected to be used as N-glycosylation sites of hp35 and hp40 subunits were replaced with unrelated codons by site-directed mutagenesis.

For the construction of glutamine mutant genes for putative N-glycosylation sites of hp40 and hp35, amino acid substitutions were performed by using PCR according to the method of Haraguchi et al (Haraguchi, et al., *J. Immunol.*, 163:2092-2098, 1999). The primers for mutagenesis were used by synthesis of nucleotides, such as T7 represented by the SEQ. ID NO.6, T3 represented by the SEQ. ID NO. 7, hp40-N125Q (S) represented by the SEQ. ID NO. 8, hp40-N125Q(AS) represented by the SEQ. ID NO. 9, hp40-N135Q(S) represented by the SEQ. ID NO. 10, hp40-N135Q(AS) represented by the SEQ. ID NO. 11, hp40-N222Q(S) represented by the SEQ. ID NO. 12, hp40-N222Q(AS) represented by the SEQ. ID NO. 13, hp40-N303OQ(S) represented by the SEQ. ID NO. 14, hp40-N303OQ(AS) represented by the SEQ. ID NO. 15, hp40-N127Q(S) represented by the SEQ. ID NO. 16, hp40-N127Q(AS) represented by the SEQ. ID NO. 17, hp40-N141Q(S) represented by the SEQ. ID NO. 18, hp40-N141Q(AS) represented by the SEQ. ID NO. 19, hp40-N251Q(S) represented by the SEQ. ID NO. 20 and hp40-N251Q(AS) represented by the SEQ. ID NO. 21. (S) and (AS) mean sense and antisense primers, respectively.

To construct single glutamine mutant genes of hp40 and hp35, T7 primer and each sense primer were used for PCR using pCIN-mp40 produced from example <2-2> or pCINmp35 produced from example <2-3> as a template. Similarly, T3 primer and each antisense primer were used for PCR. Two PCR fragments sharing a common site containing the mutational point were generated. The second PCR was performed with a mixture of these products as templates and the flanking primers, resulting in the generation of a fusion product. This product was inserted into pCI-neo plasmid. Similarly, double and triple glutamine mutant genes were constructed by using single or double glutamine mutant genes as PCR templates. Mutant genes were verified by DNA sequencing.

For the construction of mouse IL-12p70 gene containing N-glycosylation defect at Asn-220 of mp40, the region of mp40 gene in pCIN-mp35/IRES/mp40 plasmid produced from example <2-1> was replaced with mp40-N222L. In the mutagenesis experiment to construct pCIN-mp40-N222L, mp40-N220L(S) represented by the SEQ. ID NO. 22 and mp40-N220L(AS) represented by the SEQ. ID NO. 23 containing SacI site were used for PCR as primers. Amplified mutant genes were verified by treatment of restriction enzyme to specific recognition site produced after mutagenesis and DNA sequence analysis.

FIG. 2 shows amino acid composition of normal and mutant genes of human IL-12p40 or IL-12p35 subunit of the present invention. Putative N-glycosylation sites are indicated by Y shape with the number of amino acid, and amino acid substituted in each mutant gene is demonstrated in a square.

Example 4

The effect of N-glycosylation at Asn222 of Human IL-12p40

COS-7(ATCC) cells were cultured in Dulbecco's modified Eagle's medium (DMEM, GIBCO-BRL) containing 10% heat inactivated fetal bovine serum. Transfection into COS-7 cells was carried out by electroporation. The suspension of approximately $5 \times 10^6$ cells in culture medium was pulsed at 250 V, 960 µF in the presence of 20 µg of specimen DNA in addition to 2 µg of pNEB-SEAP (pNEB-secreted alkaline phosphatase, New England Biolabs), which expresses secreted alkaline phosphatase and serves as an internal control (electroporator and 0.4 electroporation cuvettes by Bio-Lad).

At 24 hours post-transfection, the medium was replaced with 1.5 Ml of serum-free CHO—SFMII medium (GIBCO-BRL). 1.5 µg/Ml of tunicamycin was added in some experiments. After incubation for another 24 hours, supernatants and cell pellets were harvested by centrifugation. Supernatants were used for the SEAP assay and cell pellets were resuspended in 200 μl of lysis solution (Promega). The levels of IL-12p70 and IL-12p40 in both supernatants and cell lysates were measured by ELISA (R&D system). For immunoblotting, 10% or 12% sodium dodecyl-sulfate-poly-acrylamide electrophoresis (SDS-PAGE) was conducted with supernatants and cell lysates. The proteins separated from the above experiment was electrotransfered to nylon membrane (Amersham). The proteins absorbed to the membrane were obtained by using biotin-labeled human IL-12 antibody (Amersham), horseradish peroxidase (HRP)-labeled streptavidin (PharMingen) and ECL kit (Amersham). The results are shown in Table 1. The levels of IL-12p70 or IL-12p40 expression were measured by ELISA and presented relatively to the level of wild type, which is arbitrarily set at 100%.

TABLE 1

The changes of expression level, secretion of IL-12p40 and IL-12p70, and IFN-γ induction capacity.

| Constructs[a] | Cell Lysates (%)[b] | | Supernatants (%)[b] | | IFN-γ induction (%)[c] |
| --- | --- | --- | --- | --- | --- |
|  | IL-12p40[d] | IL-12p70[e] | IL-12p40 | IL-12p70 |  |
| mock[f] | <1[g] | <1 | <1 | <1 | 5.2 ± 2.3 |
| hp35 + hp40 | 100 ± 8.3 | 100 ± 12 | 100 ± 13 | 100 ± 7.4 | 100 ± 11 |
| hp40 | 102 ± 11 | <1 | 91 ± 16 | <1 | 8.3 ± 2.1 |
| hp35-N127Q + hp40 | 99 ± 4.3 | 72 ± 7.7 | 98 ± 16 | 55 ± 14 | 98 ± 19 |
| hp35-N141Q + hp40 | 102 ± 18 | 90 ± 12 | 87 ± 11 | 95 ± 8.1 | 91 ± 21 |
| hp35-N251Q + hp40 | 97 ± 10 | 88 ± 8.4 | 88 ± 12 | 89 ± 8.9 | 102 ± 18 |
| hp35-N127.141Q + hp40 | 88 ± 6.7 | 71 ± 4.6 | 103 ± 13 | 52 ± 11 | 90 ± 7.9 |
| hp35 | <1 | <1 | <1 | <1 | 3.4 ± 1.4 |
| hp40-N125Q + hp35 | 89 ± 11 | 97 ± 17 | 108 ± 17 | 101 ± 11 | 108 ± 21 |
| hp40-N135Q + hp35 | 92 ± 13 | 99 ± 4.4 | 29 ± 4.7 | 102 ± 14 | 121 ± 9.1 |
| hp40-N135Q + hp35 + rhp40[h] |  |  |  |  | 97 ± 14 |
| hp40-N222L + hp35 | 90 ± 16 | 89 ± 21 | 8 ± 6.2 | 93 ± 12 | 142 ± 24 |
| hp40-N222Q + hp35 (10:10)[i] | 88 ± 17 | 90 ± 14 | 9 ± 4.3 | 94 ± 7.5 | 146 ± 12 |
| hp40-N222Q + hp35 (10:0) | 92 ± 6.7 | <1 | 10 ± 5.3 | <1 | 5.3 ± 3.1 |
| hp40-N222Q + hp35 (10:2) | 87 ± 11 | 39 ± 7.0 | 11 ± 2.7 | 48 ± 16 | 125 ± 14 |
| hp40-N222Q + hp35 (10:4) | 84 ± 14 | 62 ± 11 | 9 ± 11 | 72 ± 9.2 | 139 ± 24 |
| hp40-N222Q + hp35 (2:10) | 41 ± 4.2 | 92 ± 11 | 2.4 ± 1.0 | 91 ± 7.4 | 166 ± 19 |
| hp40-N222Q + hp35 (4:10) | 65 ± 7.8 | 99 ± 17 | 7.2 ± 0.8 | 97 ± 11 | 151 ± 23 |
| hp40-N222Q + hp35 + rhp40[h] |  |  |  |  | 103 ± 18 |
| hp40-N303Q + hp35 | 108 ± 12 | 102 ± 22 | 104 ± 11 | 121 ± 19 | 97 ± 7.8 |
| hp40-N135.222Q + hp35 | 86 ± 11 | 88 ± 6.9 | 4.0 ± 2.1 | 81 ± 8.4 | 147 ± 15 |
| hp40-N135.303Q + hp35 | 89 ± 7.1 | 97 ± 11 | 23 ± 4.5 | 82 ± 11 | 103 ± 8.3 |
| hp40-N222.303Q + hp35 | 93 ± 7.9 | 102 ± 24 | 19 ± 6.7 | 85 ± 4.8 | 125 ± 12 |
| hp40-N135.222.303Q + hp35 | 85 ± 7.4 | 65 ± 4.3 | 2.2 ± 1.1 | 65 ± 7.4 | 148 ± 28 |
| hp35-N127.141Q + hp40-N222.303Q | 89 ± 11 | 65 ± 12 | 17 ± 8.8 | 51 ± 6.5 | 120 ± 13 |
| mock[j] | <1 | <1 | <1 | <1 | 5.4 ± 3.2 |
| hp40/IRES/hp35 | 100 ± 11 | 100 ± 21 | 100 ± 14 | 100 ± 17 | 100 ± 16 |
| hp40-N222L/IRES/hp35 | 88 ± 13 | 87 ± 12 | 5.3 ± 3.2 | 95 ± 15 | 134 ± 17 |
| hp35/IRES/hp40 | 6.2 ± 2.3 | 99 ± 14 | 4.5 ± 1.9 | 101 ± 13 | 138 ± 21 |
| mp35/IRES/hp40-N222L | 5.8 ± 3.1 | 97 ± 17 | 0.3 ± 0.2 | 97 ± 16 | 169 ± 33 |
| mock[k] | <1 | <1 | <1 | <1 | 5.2 ± 2.4 |
| mp35/IRES/mp40 (mIL-12 wt) | 100 ± 17 | 100 ± 11 | 100 ± 22 | 100 ± 12 | 100 ± 22 |
| mp35/IRES/mp40-N220L (mIL-12 mut) | 94 ± 22 | 96 ± 7.9 | 2.2 ± 0.5 | 98 ± 18 | 148 ± 19 |

[a]Total 20 μg of each DNA construct was used for transfection into COS-7 cells by electroporation. For simultaneous transfection of two DNA constructs, 10 μg of each DNA construct was used.
[b]The levels of human and mouse IL-12p70 or IL-12p40 expression were measured by ELISA and presented relative to the wild-type, which is arbitrarily set at 100%.
[c]The equal amount of p70 in each mutant supernatant was used in the IFN-γ induction assay. The levels of induced IFN-γ were measured by ELISA and presented relative to the level of wild type, which is arbitrarily set at 100%.
[d]IL-12p40 indicates the monomeric and homodimeric p40 form of IL-12p40, but not the p40 part of IL-12p70.
[e]IL-12p70 indicates the heterodimer which consists of IL-12p35 and IL-12p40.
[f]The plasmid backbone used for independent expression of hIL-12p40, hIL-12p35, and their derivatives is pCIN-neo and is descibed as mock.
[g]<1 indicates values below the detectable range of ELISA assay.
[h]When the equal amount of p70 in each indicated mutant (hp40-N135Q or hp40-N222Q) and wild-type supernatant is used in IFN-γ induction assay, the insufficient hp40 in each mutant supernatant compared to wild-type supernatant was reconstituted with hp40 supernatant obtained after tranfection with hp40 only
[i]Numbers in ( ) mean each amount (μg) of cotransfected plasmid, pCIN-hp40-N222Q and pCIN-hp35. Total 20 μg of DNA was cotransfected and insufficient amount of DNA was supplemented with pCI-neo plasmid.
[j]The plasmid backbone used for co-expression of hIL-12p40 and hIL-12p35 or their derivatives is pGX0 and is described as mock.
[k]The plasmid backbone used for co-expression of mIL-12p40 and mIL-12p35 or their derivatives is pTV2 and is described as mock.

As seen in TABLE 1, mutation of Asn-141 of p35 and Asn-303 of p40 had no effect on IL-12p70 or IL-12p40 secretion. But, the secretion of IL-12p40 in Asn-135 and Asn-222 mutants was decreased. Especially, Asn-222 mutant showed same result when its amino acid was replaced with leucine (Leu) or glutamine (Gln), indicating the loss of N-glycosylation at Asn-222 is very important.

Figure 3A:
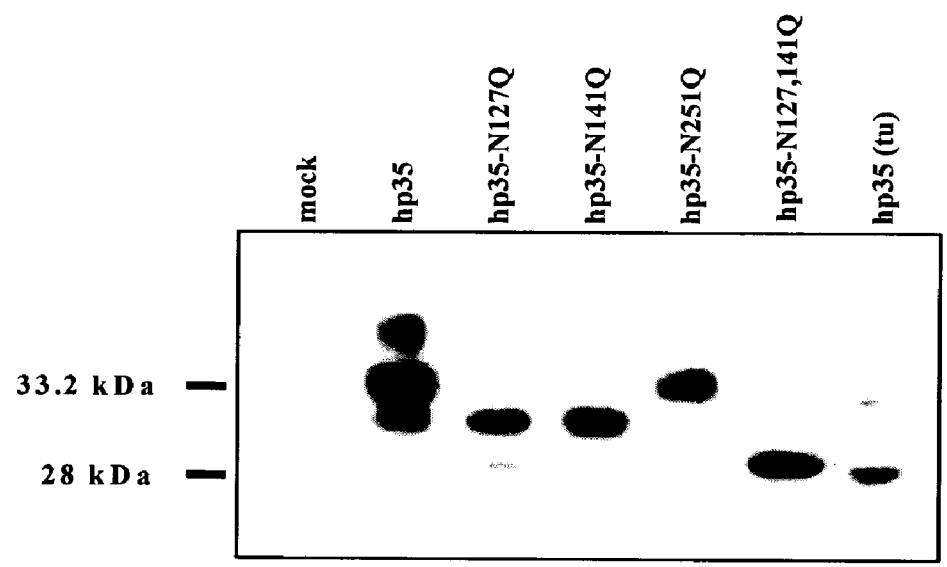
FIG. 3a shows a result of western blot analysis of human IL-12p35 and its derivatives with mutations at putative N-glycosylation sites in cell lysate of the present invention.

FIG. 3a shows immunoblotting results of cell lysates after that wild type and mutant human IL-12p35 genes were transfected into COS-7 cells. Column 1 and 2 show results from cell lysates transfected with pCI-neo and pCIN-hp35 respectively. Column 3, 4, 5 and 6 show results from cell lysates transfected with expression vectors containing mutant gene such as pCIN-hp35-N127Q, pCIN-hp35-N141Q, pCIN-hp35-N251Q and pCIN-hp35-N127,251Q respectively. About 33.2 kDa band in column 2 and 5 is the protein of N-glycosylated p35 subunit. When N-glycosylation was inhibited by tunicamycin, as shown in column 3 and 4, 28 kDa band was formed. Therefore, Asn-127 and Asn-141 amino acids are the N-glycosylation site.

Figure 3B:
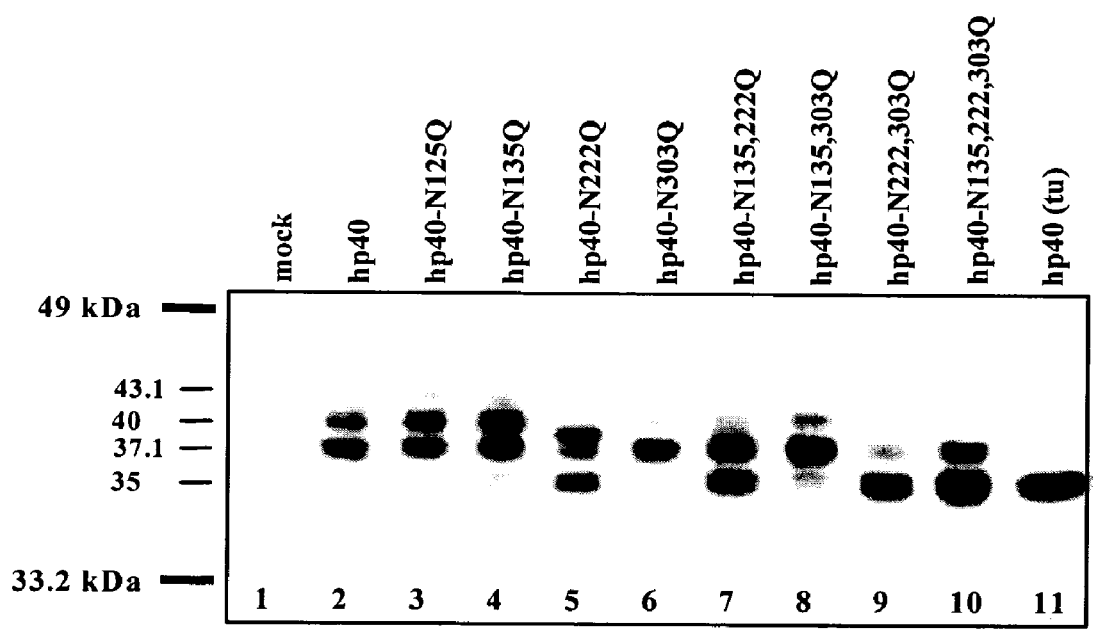
FIG. 3b shows a result of western blot analysis of human IL-12p40 and its derivatives with mutations at putative N-glycosylation sites in cell lysate of the present invention.

FIG. 3b shows immunoblotting results of cell lysates obtained from COS-7 cells transfected with wild type and mutant human IL-12p40 genes. Column 1 and 2 show results from cell lysates transfected with pCI-neo and pCIN-hp40 respectively. Column 3, 4, 5 and 6 show results from cell lysates transfected with expression vectors containing mutant gene such as pCIN-hp40-N125Q, pCIN-hp40-N135Q, pCIN-hp40-N222Q and pCIN-hp40-$N_3O_3Q$ respectively. Again, column 7, 8, 9 and 10 show results of cell lysates transfected with double or triple mutant genes. A result of cell lysates transfected with pCIN-hp40 and tunicamycin, an antagonistic agent against N-glycosylation, is shown in column 11.

In many reports, 3-4 bands having 36-45 kDa are known in immunoblot assay of IL-12p40. Similarly, 36, 37.5, 40 and 43.1 kDa bands are shown in immunoblot assay of cell lysates transfected with wild type IL-12p40 and IL-12p35. In cell lysates treated with tunicamycin, only 36 kDa band was remained while the other three bands were disappeared (Column 11). So, this band is p40 subunit which is not N-glycosylated. Bands obtained from Asn-125 or Asn-135 mutation, were almost same as those of wild type (Column 3, 4). Bands were shifted in Asn-222 and Asn-303 (Column 5, 6), indicating amino acids of 135, 222 and 303-Asn are the N-glycosylation site.

Figure 3C:
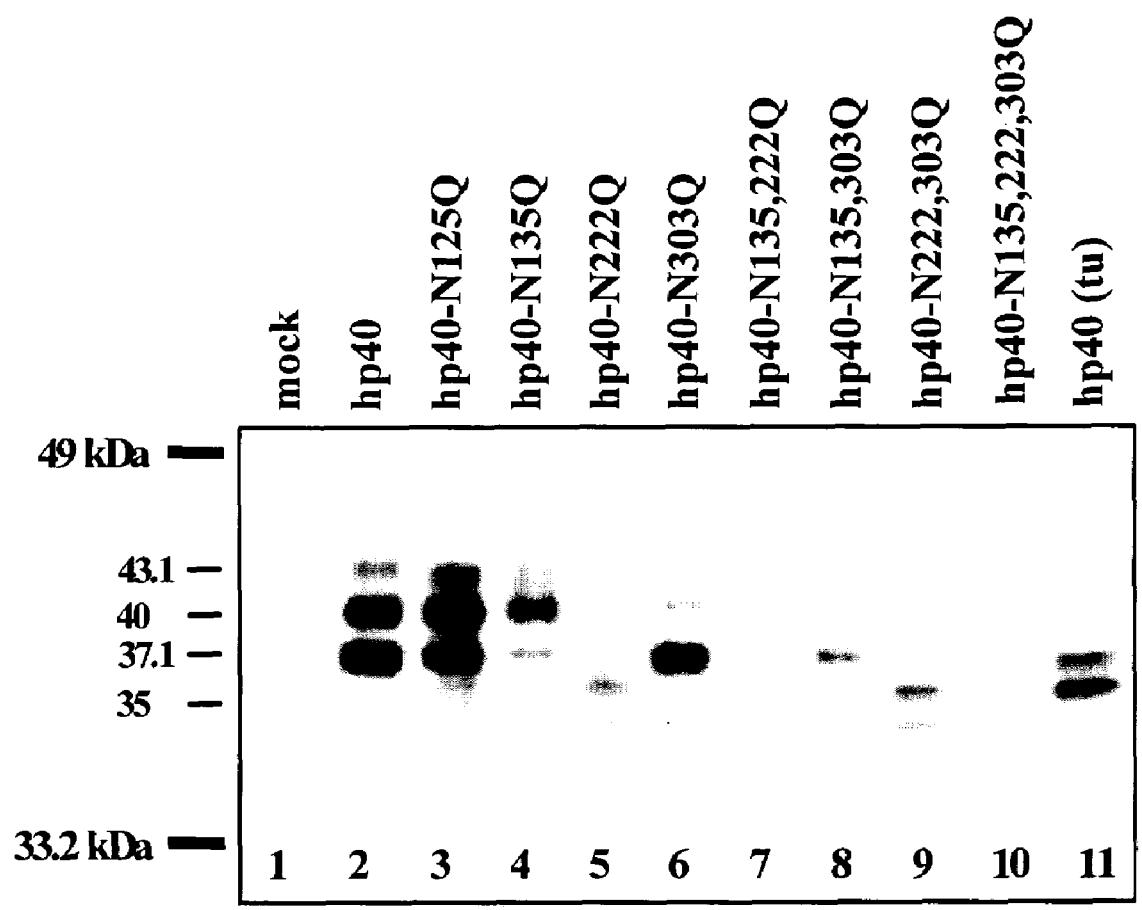
FIG. 3c shows a result of western blot analysis of human IL-12p40 and its derivatives with mutations at putative N-glycosylation sites in cell supernatant of the present invention.

FIG. 3c shows immunoblotting results of supernatants obtained from COS-7 cell culture transfected with wild type and mutant human IL-12p40 genes. Explanations for each column are same as FIG. 3b. Similar to the result of cell lysates, 3-4 bands having 36-45 kDa were made. Bands obtained from Asn-125 or Asn-135 mutation, were almost same as those of wild-type (Column 3, 4). Bands were shifted in Asn-222 and Asn-303(Column 5, 6). Especially, Asn-135 and Asn-222 mutants were not secreted to the cell culture medium, contrary to the results of cell lysates. This result is consistent with the quantification result obtained by ELISA.

Expression vectors, pGX0-hp35/IRES/hp40-N222L and pGX0-hp40-N222L/IRES/hp35, containing mutant gene of the present invention in which Asn-222 is replaced with Leu-222, were deposited at Gene Bank of Korea Research Institute of Bioscience and Biotechnology on Feb. 29, 2001(Accession No: KCTC 0969BP and KCTC 0970BP).

<4-1> The Effect of N-Glycosylation of hp35 on the Synthesis, Heterodimerization, and Secretion of hIL-12p70.

The effect of N-glycosylation of hp35 on the synthesis, heterodimerization, and secretion of hIL-12p70 was analyzed by ELISA with both culture supernatants and lysates of cells transfected with hIL-12 expression vectors including wild type hp35 gene or its N-glycosylation mutant genes.

As seen in TABLE 1, the removal of potential N-glycosylation residues of hp35, except for Asn-127, did not significantly affect the synthesis, heterodimerization and secretion of hIL-12p70. However, deglycosylation of Asn-127 was shown to decrease the heterodimerization and secretion of hIL-12p70 to some degree, since the expression levels of hp35-N127Q and hp35-N127,141Q on western blot, in which transfection efficiency was normalized, were similar to those of other mutants. Accordingly, these results indicate that the N-glycosylation at Asn-127 of hp35 is important for the heterodimerization and secretion of hIL-12p70, but not at Asn-141.

<4-2> The Effect of N-Glycosylation of hp40 on The Synthesis, Heterodimerization, and Secretion of hIL-12p70

To determine the effect of N-glycosylation of hp40 on the synthesis, heterodimerization, and secretion of hIL-12p70, the levels of hIL-12p70 and hIL-12p40 existing in both culture supernatants and lysates of cells transfected with hIL-12 expression vectors including wild type hp40 gene or its N-glycosylation mutant genes were analyzed by ELISA.

Mutation of Asn-135 or Asn-222 had little effect on hIL-12p70 secretion, as seen in TABLE 1, because the extracellular level of hIL-12p70 of these mutants was similar to that of wild type hp40. Interestingly, the secretion of hIL-12p40 in Asn-135 and Asn-222 mutants was significantly decreased, specially, Asn-222 mutant showed the secretion level less than about 9% compared with that of wild type hp40, indicating that N-glycosylation at Asn-222 is required for the secretion of hIL-12p40 alone, but not heterodimeric hIL-12, hIL-12p70. Also, double and triple mutants containing Asn-135 and/or Asn-222 showed the low level of hIL-12p40, but not that of hIL-12p70. In contrast, the other mutants appeared to produce an equal amount of hIL-12p40 and hIL-12p70 in cell lysates compared with wild type hp40. The mutations of Asn-1245 and Asn-303 did not cause significant difference in the expression, heterodimerization and secretion of hIL-12p40 and hIL-12p70.

As a whole, these data indicate that N-glycosylation of hp40 at Asn-222 is critical for the secretion of IL-12p40 but not required for the heterodimerization and secretion of IL-12p70, whereas N-glycosylation of hp35 at Asn-127 is important for the heterodimerization and secretion of IL-12p70. It is also consistent with the report that N-glycosylation of hp35 appears to be a key requirement for the secretion of IL-12p70 (Carra, G., et al., J. Immunol., 164: 4752-4761, 2000).

<4-3> The Effect of N-Glycosylation of hIL-12 on its Biological Activity

To investigate the role of N-glycosylation of hIL-12 on its biological activity, the IFN-γ induction ability of wild type hIL-12 and its derivatives with mutation at putative N-glycosylation sites was analyzed. The culture supernatants containing equal amount of wild-type hIL-12p70 and its mutants, 100 ng/Ml each, were incubated with human PBLs. The level of induced IFN-γ (in each culture supernatant was determined by ELISA. As seen in TABLE 1, there was little difference between wild-type and all of its derivatives in terms of IFN-γ induction. However, hp40 derivatives mutated at Asn-135 and/or Asn-222 showed some increased IFNγ induction compared with wild-type or the other hp40 mutants. It is probably due to the fact that the level of hIL-12p40, which was known to be an antagonist of hIL-12p70, in culture supernatants of mutants containing hp40-N135Q and/or hp40-N222Q was relatively very lower than that of the other mutants.

Example 5

Role of IL-12p35 in Secretion of IL-12p70 Containing Mutated Glycosylation

To investigate how deglycosylation at Asn-222 of hp40 decreases the secretion of hIL-12p40, but not that of hIL-12p70, present inventors co-transfected the restricted amount of hp40-N222Q-expressing plasmid with the various amount of wild-type hp35 DNA.

Human peripheral blood mononuclear cells (PBMC) were isolated by Ficoll-Hypaque (Sigma) density gradient centrifugation from fresh blood and resuspended in RPMI-1640 medium (GIBCO-BRL) supplemented with 10% heat inactivated FBS and penicillin/streptomycin (GIBCO-BRL). For the human IFN-γ induction assay, human PBM cells ($4\times10^5$) were incubated with culture supernatants containing 100 ng/Ml of human IL-12p70 or its mutant derivatives for 16 hours.

For the mouse IFN-γ detection, spleens of 6 to 8 weeks old female BALB/c mice were obtained and $1\times10^5$ splenocytes were incubated with culture supernatants containing 100 ng/Ml of mouse IL-12p70 or its mutant derivatives for 24 hours. The amounts of induced human and mouse IFN-γ were estimated by human and mouse IFN-γ ELISA kit (R&D systems), respectively. The results are given in TABLE 1. The numbers in TABLE 1 is the amount of IFN-γ measured by ELISA and presented relative to the level of wild type, which is arbitrarily set at 100%.

Generally, it was known that p35 subunit is not secreted alone and is secreted as a form of IL-12p70 in association with p40 subunit, whereas p40 subunit is secreted in the form of either monomer or homodimer, suggesting that p40 subunit is the major factor in the secretion of IL-12p70. As shown in TABLE 1, the secretion level of hIL-12p70 increased in proportion to the amount of transfected hp35 DNA in the case of both wild-type hp40 and hp40-N222Q. This result indicates that hp40 subunit with secretion defect is secreted in the form of IL-12p70 if it is associated with hp35 subunit, suggesting that hp35 subunit also gives another help to the secretion of hIL-12p70. Recently, the report that the conformational change in hp40 subunit happens upon the binding of hp35 suggests the possibility for the contribution of hp35 subunit to IL-12p70 secretion (Yoon, C. et al., *EMBO J.,* 19:3530-3534, 2000). On the basis of this report and the data of the present invention, it is verified that hp40 containing deglycosylation at Asn-222 is defect in the secretion of itself but can be secreted in the association with hp35 due to the conformational change of the hp40 region and subsequent exposure or generation of covered or new secretion signal, respectively.

Example 6

Construction of HCV-E2 DNA Vaccine and Expression Vector Containing Mouse IL-12p40 Asn-220 Mutant Gene <6-1> Construction of pCIN-mp40-N220L To inspect the possibility for the use of hIL-12 mutant gene of the present invention in gene therapy as a DNA vaccine, the sequence of mouse IL-12p40(mp40) gene homologous to Asn-222 of hp40 gene was searched. Asn-220 of mp40 was located in the very similar context to that of Asn-222 of hp40, but this amino acid was not known to be N-glycosylated until now. Therefore, the inventors generated the mutant mp40 gene, mp40-N220L, in which Asn at 220 in amino acid sequence was replaced with Leu by site-directed mutagenesis. For mutagenesis, SEQ. NO. 22 and SEQ. NO. 23 were used as primers. For easy identification of mutant gene, SacI restriction site was generated. Amplified mutant genes were verified by the treatment of restriction enzyme to specific recognition site produced after mutagenesis and DNA sequence analysis. Eventually, the pCIN-mp40-N220L vector containing mouse IL-12p40 mutant gene which can be expressed in animal cells was constructed.

<6-2> Construction of pTV2-mp35/IRES/mp40-N220L Vector

To generate a vector encoding mouse p35 and p40 subunits and being used for the DNA immunization, pTV2 vector, an eukaryotic expression vector used as a DNA vaccine vector in small animals (Lee, et al., *J. Virol.,* 72:8430-8436, 1998; Cho, et al., *Vaccine,* 17:1136-1144, 1999), was treated with Asp718 and Not I. pTV2-mp35/IRES/mp40 vector was constructed by inserting mp35/IRES/mp4O fragment obtained from pSK-mp35/IRES/mp40 treated with restriction enzymes into therein. And, pSK-mp35/IRES/mp40-N220L vector containing Asn-220 mutant gene, which can express p35, was generated by inserting mp40-N220L fragment into pSK-mp35/IRES/mp40 treated with NcoI and NotI. To delete mp40 fragment, pTV2-mp35/IRES/mp40 vector was treated with EcoRV and NotI, followed by added mp40-N220L. As a result, the pTV2-mp35/IRES/mp40-N220L was constructed.

The pTV2-mp35/IRES/mp40-N220L vector of the present invention was deposited at Gene Bank of Korea Research Institute of Bioscience and Biotechnology on Feb. 29, 2000 (Accession No: KCTC 0745BP).

<6-3> Construction of pTV2-HCV-E2 Vector pTV2-HCV-E2 DNA vaccine vector which can express HCV-E2 protein in eukaryotic cells was constructed (Song M. K., et al., *J. Virol.,* 74:2920-2925, 2000). As seen in FIG. 4, pTV2-HCV-E2 DNA vaccine vector is consist of simian virus 40 replication origin (SV40 ori), cytomegalovirus (CMV) promoter, tripartite leader sequence (TPL) of adenovirus, multiple cloning sequence (MCS), SV40 polyadenylation sequence (poly A) and ampicillin resistance gene (AmpR). And also, HCV-E2 gene is cloned in MCS of this vector. Carboxyl-terminal (C-terminal) containing hydrophobic amino acid residue of E2 gene used in the present invention was removed to facilitate protein secretion. And to help protein expression and cell secretion, aminocyl-terminal (N-terminal) and signal sequence(s) of herpesvirus (HSV) glycoprotein D(gD) were linked.

<6-4> Secretion of IL-12p40 and IL-12p70 According to the Mutation of Mouse IL-12p40 Asn-220

Vectors listed in TABLE 1 were transfected into COS-7 cells using the same method in <Example 4>. The culture supernatants and cell lysates were analyzed through ELISA (PharMingen). Expression levels of wild-type IL-12p70 and 40 were shown in TABLE 1. <1 in pCI-neo means that proteins were not detected by ELISA.

As seen in TABLE 1, mp40-N220L mutants showed the similar characteristics to Asn-222 mutant of hp40 in the point of the secretion of IL-12p40 and IL-12p70 and its biological activity.

To apply the mp40-N222L mutant gene into the DNA vaccine model and to compare it with wild-type mp40 gene in a view of the induction of Th1 and CTL immune responses, this inventors inserted mp35/IRES/mp40 (mIL-12 wt) or mp35/IRES/mp40-N220L (mIL-12mut) genes into the pTV2 DNA vaccine vector and observed their characteristics in vitro. In result, as seen in TABLE 1, mIL-12mut (mp40-N220L mutant) gene in pTV2 vector also showed the similar characteristics to Asn-222 mutant of hp40 in the point of the secretion of IL-12p40 and IL-12p70 and its biological activity.

Example 7

Effect of Mutant IL-12 on Antigen-Specific Humoral Immune Response

In a previous report, DNA vaccination of plasmid encoding HCV-E2 antigen (pTV2-gDsE2t) was sufficient to induce the antigen-specific humoral and cell-mediated immune responses after 3 weeks post-immunization (Song, M. K. et al., *J. Virol.*, 74:2920-2925, 2000). To determine whether the mIL-12mut gene also can affect the efficient antigen-specific immune response in vivo compared with mIL-12 wt gene, mice were initially immunized and boosted with pTV2-mIL-12mut or pTV2-mIL-12 wt, together with pTV2-gDsE2 plasmid 4 weeks later.

To inspect the induction of immune response by DNA vaccine with expression vector containing mutant genes of the present invention, 6 to 8-weeks old BALB/c mice were immunized with various pTV2 or pTV2-gDsE2t DNAs with mutant mIL-12 or wild-type mIL-12 DNAs. Particularly, the anterior tibialis muscles of each mouse were injected with a total 200 μg of DNA, formulated in a final volume of 100 μl of phosphate-buffered saline and boosted on time with an identical dose of DNA at 4 week interval. Humoral immune responses were monitored 3 weeks after booster immunization by ELISA. In particular, 100 ng of hghE2t protein, which is a fusion protein of human growth hormone (hgh) and C-terminal truncated HCV E2(HCV E2t), was coated to each well of 96-well plate (Dynex Technologies). Sera from immunized mice were diluted to 1:100 for reaction with hghE2t protein and introduced to the determination of relative levels of HCV E2t-specific IgG, and its subclasses, such as IgG1 and IgG2a.

As shown in FIGS. 5a, 5b, 5c and 5d, HCV E2 DNA vaccine induced systemic HCV E2-specific total IgG, IgG1 and IgG2a levels significantly higher than negative control values, and co-injection with mIL-12mut gene or mIL-12 wt gene showed the similar total IgG level compared to HCV E2 DNA vaccine only. And, the level of IgG1 was similar among the groups injected with HCV E2 DNA. In contrast, the level of IgG2a against HCV E2 slightly increased in mIL-12 wt group and significantly increased in mIL-12mut group compared with HCV E2 DNA immunized only group. In addition, the ratio of IgG2a/IgG1, which is generally accepted as an indirect indicator of Th1 immunity, was the highest in the mIL-12mut group, which showed the similar pattern of IgG2 level. These data represent that mIL-12mut gene significantly affected the shift of IgG subclasses from IgG1 to IgG2a in humoral immune response compared with mIL-12 wt or HCV E2 only group, suggesting that IL-12mut may induce Th1 type immune response.

Example 8

Cell-Mediated Immune Response of Immunized Mice

<8-1> Induction of Antigen-Specific Th1 Immune Response by Mutant IL-12

To investigate the effect of mIL-12mut gene on Th1 immune response, which is one of the parameter used to evaluate the potency of cell mediated immunity, IFN-γ expression of splenocytes was measured. $1 \times 10^5$ splenocytes obtained at 8 weeks after the booster immunization were added to wells of U-bottomed 96-well plate. Then, 1 or 5 μg of hgh-E2t protein purified from CHO cells was added to each well and the cells were incubated at 37° C., in 5% $CO_2$ incubator for 3 days. And then, cell supernatants were secured and used for the detection of IFNγ levels using ELISA kit (R&D systems). It was known that IFNγ induced after stimulation with specific antigen is produced from antigen-specific CD4+ T cell and it is the indicator of Th1 immune response.

Figure 6:
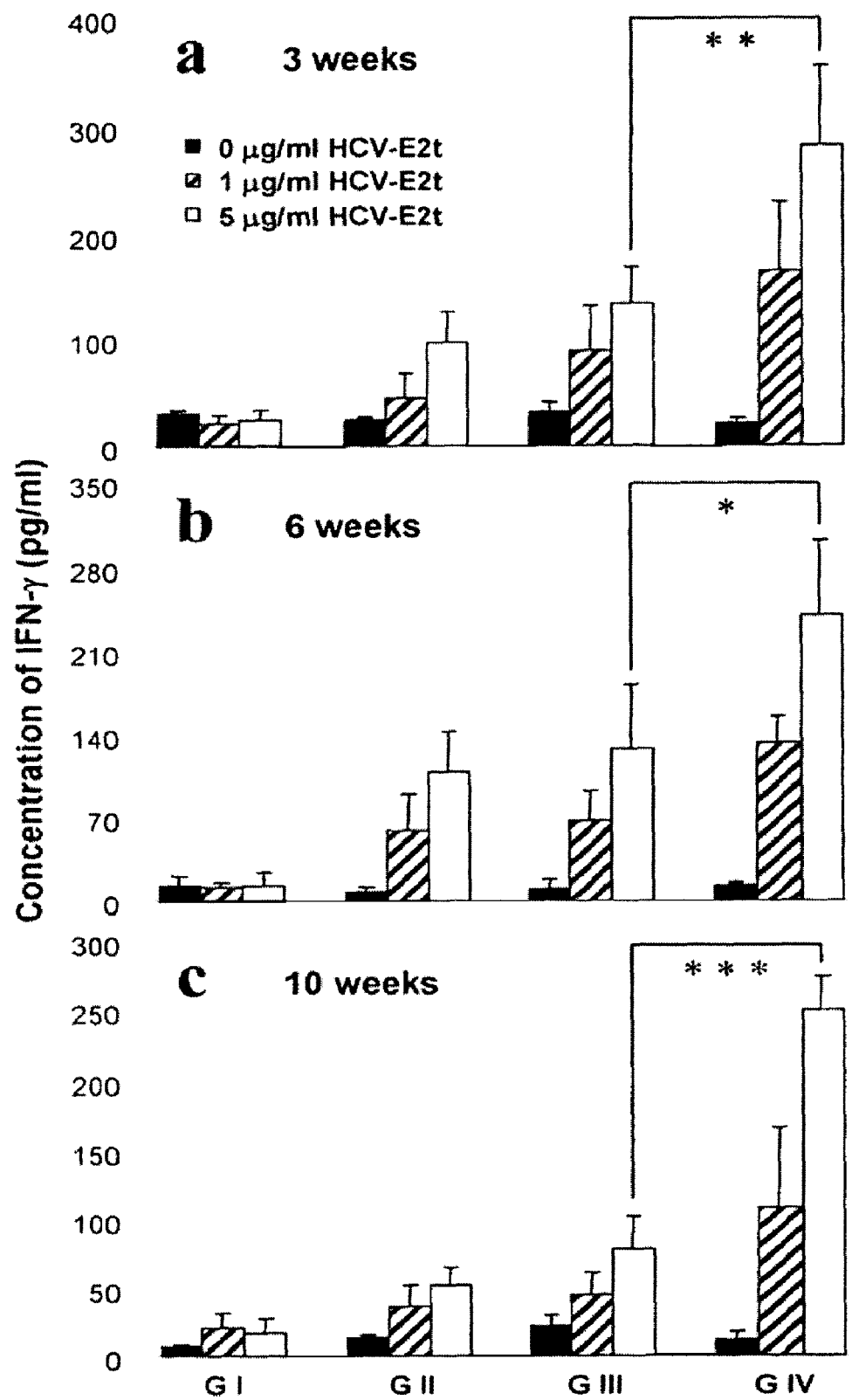

As shown in FIG. 6, HCV E2 DNA immunized group without cytokine gene showed the increased level of IFN-γ in proportion to the concentration of hghE2t protein, whereas mock plasmid immunized group did not. Expectedly, the level of IFN-γ induction in mIL-12 wt group was more enhanced than in HCV E2 only group, and mIL-12mut group showed up to 2-3 times higher production of IFN-γ than mIL-12 wt group, suggesting that mIL-12p70 increases the antigen-specific Th1 immune response and mIL-12p40 inhibits the induction of Th1 immune response by IL-12p70 in vivo.

<8-2> Long-Term Enhancement of Antigen-Specific CD8+ T Cell Function by Mutant IL-12

As noted above, mIL-12mut gene contributed to the long-term Th1 immune response in HCV E2 DNA immunization. To determine whether the long-term Th1 immune response induced by the expression of mIL-12mut gene correlates with CTL immunity and the major cell-mediated immune response, and therefore mIL-12mut gene can affect the maintenance of CTL activity in DNA immunization model, the present inventors performed the CTL assay with splenocytes of DNA immunized mice at various weeks after booster immunization. Splenocytes ($2 \times 10^7$) were restimulated in vitro at 37° C. with mitomycin C-treated (25 μg/Ml) CT26-hghE2t cells ($1 \times 10^6$), which express truncated form of HCV envelope protein 2 (E2t). After 5 days in vitro culture, effector cells were tested in a conventional cytotoxicity assay against different target cell, such as CT26-hghE2t or CT26-neo. Various numbers of effector cells were plated in triplicate to achieve the desired E/T ratio. $^{51}$Cr-labled target cells ($5 \times 10^3$) were added to each well of U-bottomed 96-well plate, and after 6 hours incubation at 37° C., the supernatant was harvested and counted with a γ-counter (Wallac, Turku, Finland). The percentage of specific lysis was calculated as following mathematical formula 1. Minimum lysis was obtained by incubating the target cells with the culture medium alone. Maximum lysis was obtained by exposing the target cells to 1% Nonidet-P40.

<Mathematical Formula 1>

Percentage of specific lysis=(Experimental lysis−Minimum lysis)×100/(Maximum lysis−Minimum lysis)

As a result, as shown in FIG. 7, two weeks after boost, all groups except for mock plasmid immunized group showed very strong antigen-specific CTL activity. However, there was little difference among HCV E2 only, mIL-12 wt and mIL-12mut groups. CTL response was induced more in mIL-12 wt coimmunized group than in HCV E2 only group in overall period, indicating that mIL-12 gene played a role in the enhanced CTL generation. Interestingly, the difference in CTL activity between mIL-12mut group and the other two groups, HCV E2 only and mIL-12 wt group, became bigger and bigger as the time after booster immunization was longer. Especially, at 10 weeks, CTL response was very low in HCV E2 only and mIL-12 wt groups, suggesting that the frequency of antigen-specific CTL decreased significantly after long period, whereas mIL-12mut group showed 5 to 10 times higher CTL activity than the other two groups sustaining the antigen-specific CTL response. As a control, when CT26-neo cell was used as the target cell, no lysis was observed in all groups, suggesting that CTL activity observed in this experiment is HCV E2-specific.

<8-3> FACSCalibur Flow Cytometry Analysis for IFN-γ Production of CD8+ Cells of Immunized Mice To investigate whether the long-term enhancement of CTL activity is originated from the frequency of antigen-specific CD8+ T cell, and for determination of CD8+ antigen-specific T lymphocyte frequency, following experiment was performed. Splenocytes ($2 \times 10^7$) obtained at the indicated week after the booster immunization were stimulated with CT26-hghE2t cells ($1 \times 10^6$) in the presence of 10 U/Ml recombinant IL-12(PharMingen) for 40 hours, and then 4 μl of GolgiStop™ (PharMingen) was added and the cells were incubated for another 8 hours at 37° C. For the direct purification of CD8+ T cells, the stimulated splenocytes were incubated with anti-CD8 microbeads (Miltenyi Biotech, Inc) and then passed through a column of miniMACS system (Miltenyi Biotech, Inc), and the remaining CD8+ T cells were isolated. To block nonspecific staining, cells were preincubated with Fc Block™ (PharMingen) and stained with FITC-conjugated anti-mouse CD8. After the incubation, the cell suspensions were fixed and permeablized with Cytofix/Cytoperm™ (PharMingen) before adding PE-conjugated anti-mouse IFN-γ mAb or control PE-conjugated isotype-matched mAb. Stained cells were analyzed by FACSCalibur flow cytometry (Becton Dickinson), and then induction of IFN-γ was observed.

TABLE 2

Frequency kinetics of HCV-E2-specific precursor CD8+ T cells

| | | Frequency of HCV-E2-specific CD8+ T cells | | | | | | | |
|---|---|---|---|---|---|---|---|---|---|
| | | Intracellular IFN-γ staining assay (%)[c] | | | | Limiting dilution assay (No.)[d] | | | |
| | | Group[b] | | | | | | | |
| No. of immunization[a] | Weeks after final immunization | I | II | III | IV | I | II | III | IV |
| 2 | 0 | 0.08 | 0.34 | 0.42 | 0.58 | 7.1 | 36.1 | 39.0 | 47.1 |
| | 3 | 0.05 | 0.34 | 0.48 | 0.72 | 8.4 | 39.0 | 48.8 | 66.7 |
| | 6 | 0.06 | 0.29 | 0.39 | 0.73 | 6.9 | 34.8 | 46.8 | 64.9 |
| | 10 | 0.07 | 0.21 | 0.20 | 0.68 | 7.2 | 18.2 | 19.8 | 64.3 |
| | 14 | 0.07 | 0.09 | 0.09 | 0.57 | 8.1 | 9.6 | 8.8 | 45.7 |
| 1 | 4 | 0.06 | 0.33 | 0.42 | 0.55 | 7.5 | 33.2 | 41.0 | 48.7 |
| | 8 | 0.08 | 0.26 | 0.27 | 0.51 | 8.4 | 11.3 | 12.5 | 48.2 |
| | 14 | 0.06 | 0.10 | 0.07 | 0.42 | 7.1 | 6.8 | 8.1 | 44.7 |

[a]Six- to 8-week-old female BALB/c mice were immunized with various plasmids of the present invention at 4-week interval.
[b]The expression of each group is as follows. Group I; pTV2, Group II; pTV2-HCV-E2t+pTV2, Group III; pTV2-HCV-E2t+pTV2-mIL-12wt, Group IV; pTV2-HCV-E2t+pTV2-mIL-12mut
[c]$2 \times 10^7$ of splenocytes obtained from DNA-immunized mice were restimulated with $1 \times 10^6$ of mitomycin C-treated CT26-hghE2t cells in vitro. After 48 hours in culture, CD8+ T cells were isolated by using MACSing. After fixation and permeabilization, the cells were stained with anti-CD8 and anti-IFN-γ antibody. Live CD8+ T cells were gated by plotting of cells with FSC and CD8 and then, the percentage of IFN-γ-producing CD8+ T cells among live CD8+ T cells was calculated by plotting of live CD8+ T cells with CD8 and IFN-γ. Data are represented as the average value obtained with 2 mice per group in two independent experiments.
[d]Splenocytes obtained from DNA-immunized mice were diluted, mixed with mitomycin C-treated CT26-hghE2t cells, and incubated for 5 days. The specificity of resulting CTL was determined by specific lysis of $^{51}$Cr-labeled CT26-hghE2t cells. Wells were scored as positive for CTL recognition if the level of specific lysis exceeds the mean lysis value plus 3SD obtained from naive mice. The frequency of precursor CTL per $1 \times 10^7$ spleen cells was calculated by regression analysis of the number of negative wells at each dilution of responder cells. Data are represented as the average value obtained with 2 mice per group in two independent experiments.

As shown in TABLE 2, mice coimmunized with mIL-12mut gene had a 3 to 7-fold enhancement in the frequency of CD8+ IFN-γ producing cells compared with HCV E2 only and mIL-12 wt groups at 0, 3, 6, 10 or 14 weeks after booster immunization, correlating with the result in CTL response. By contrast, in isotype-matched control experiment, there was no difference among all groups. Like the result of CTL assay, the frequency of IFN-γ producing CD8+ T cells among immunization groups was not much different at 2-3 weeks after booster immunization. These data demonstrate that the expression of mIL-12mut gene sustained the frequency of CD8+IFN-γ producing T cells after DNA immunization for long period. In this regard, it might be suggested that in vivo role of IL-12p70 itself in cell-mediated immune response is the long-term maintenance of Th1 and CTL, whereas IL-12p40 inhibits the IL-12p70 as an antagonist in vivo.

<8-4> The Frequency of Antigen-Specific CD8+ T Cells of Splenocytes of Immunized Mice To investigate the frequency of other antigen-specific CD8+ T cells, limiting dilution assay (LDA) was conducted. In this experiment, the frequency of antigen-specific CD8+ T cells was measured by using lysis ability of HCV E2 specific CD8+ T cells (Kuzushima, K. et al., Blood, 94:3094-3100, 1999). Splenocytes of booster immunized mice were diluted with various concentration, and placed into wells of U-bottomed 96-well plate to 20 wells/dilution. CT-26 cells expressing E2, were treated with mytomycin C (500 μg/Ml) to block cell division, and activated with diluted splenocytes for 5 days. $^{51}$Cr-labeled target cells (5×10$^3$) were added to each well of the above well plate, and after 6 hours at 37° C., the supernatant was harvested and counted with a γ-counter (Wallac, Turku, Finland). CTL frequency was calculated and regarded as positive when the level of specific lysis was higher than that of mean lysis value+3× standard deviation (Kuzushima, K. et al., *Blood*, 94:3094-3100, 1999).

The result of limiting dilution assay was similar to the result of intracellular staining assay. Namely, the highest frequency of antigen-specific CD8+ T cell was observed in mIL-12 group even in early stage of immunization, and this frequency had been remained over 14 weeks after booster immunization (TABLE 2).

<8-5> Enhancement of Protective Immune Response by Mutant IL-12

To confirm the Th1 and CTL immunity induced by mIL-12mut gene in vivo, and to examine that the correlation of protective immunity with Th1 and CTL immunity, CT26-hghE2t tumor cells expressing hghE2t were injected in the groups of the immunized mice at 12 weeks after the booster immunization. 2 weeks after, relative levels of antigen-specific IgG, IgG1, IgG2 and the ratio of IgG2a/IgG1 were determined, and the size of tumor was measured for 30 days. Particularly, the mean local tumor growth was determined by measuring the volume and diameter of tumors with calipers every three days. Also, the survival rates of these mice were determined by observing for about 70 days.

As shown in FIGS. 8a, 8b and 8c, the group of mice immunized with mIL-12mut induced strong Th1 immune response. The group of mIL-12 wt immunization displayed the delayed tumor growth in contrast to the group of only pTV2-gDsE2t immunization, whereas the group of mIL-12mut immunization showed the significantly delayed tumor growth. In control group, most of mice had tumor and died within 50 days, but 90% of mice in the group of mIL-12mut could survive after 70 days. Thus, These data suggest that HCV E2-specific Th1 and CTL responses induced by mIL-12mut gene confers in vivo protection against the challenge of modified tumor cells expressing specific antigen. Although it is not easy to evaluate relative effects of Th1 and CTL responses on tumor protection in vivo, it is likely that E2-specific CD8+ CTLs and Th1 cells could directly kill the CT26-hghE2t cells and help the CTLs, respectively as shown in the in vitro Th1 and CTL assay. Also, IgG2a antibodies, which strongly binds to FcγR on macrophages and natural killer cells, might mediate antibody-dependent cell-mediated cytotoxicity.

INDUSTRIAL APPLICABILITY

As described hereinbefore, the present invention relates to the IL-12p40 subunit mutant gene which can produce interleukin 12 (IL-12) of human and mouse origin with high activity, and the expression vector including above mutant gene as well as the use of them to DNA vaccine adjuvant. Particularly, it relates to IL-12p40 mutant gene which inhibits the secretion of IL-12p40 but normally secretes active IL-12p70 by making mutation at Asn-222 (human) or Asn-220 (mouse) amino acid of IL-12p40, which acts as a competitive inhibitor of active form of IL-12, IL-12p70. IL-12p40 mutant gene of the present invention can induce optimal cell-mediated immune response at early stage and for a long time if immunized with DNA vaccine. Therefore, the IL-12p40 mutant gene of the present invention can be useful for DNA vaccination and gene therapy to various diseases, for example, AIDS, hepatitis C or hepatitis B, cancer, influenza, tuberculosis and malaria, which essentially require cellular immune responses for their therapy. Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended claims.

SEQUENCE LISTING

<160> NUMBER OF SEQ ID NOS: 25

<210> SEQ ID NO 1
<211> LENGTH: 1007
<212> TYPE: DNA
<213> ORGANISM: Homo sapiens

<400> SEQUENCE: 1

```
agcaagatgt gtcaccagca gttggtcatc tcttggtttt ccctggtttt tctggcatct      60 ccctcgtgg  ccatatggga actgaagaaa gatgtttatg tcgtagaatt ggattggtat     120
ccggatgccc ctggagaaat ggtggtcctc acctgtgaca ccccctgaaga agatggtatc     180 acctggacct tggaccagag cagtgaggtc ttaggctctg gcaaaaccct gaccatccaa     240
gtcaaagagt ttggagatgc tggccagtac acctgtcaca aaggaggcga ggttctaagc     300
cattcgctcc tgctgcttca caaaaaggaa gatggaattt ggtccactga tattttaaag     360
```

```
gaccagaaag aacccaaaaa taagaccttt ctaagatgcg aggccaagaa ttattctgga    420
cgtttcacct gctggtggct gacgacaatc agtactgatt tgacattcag tgtcaaaagc    480
agcagaggct cttctgaccc ccaagggtg acgtgcggag ctgctacact ctctgcagag     540
agagtcagag gggacaacaa ggagtatgag tactcagtgg agtgccagga ggacagtgcc    600
tgcccagctg ctgaggagag tctgcccatt gaggtcatgg tggatgccgt tcacaagctc    660
aagtatgaaa actacaccag cagcttcttc atcagggaca tcatcaaacc tgacccaccc    720
aagaacttgc agctgaagcc attaaagaat tctcggcagg tggaggtcag ctgggagtac    780
cctgacacct ggagtactcc acattcctac ttctccctga cattctgcgt tcaggtccag    840
ggcaagagca agagagaaaa gaaagataga gtcttcacgg acaagacctc agccacggtc    900
atctgccgca aaaatgccag cattagcgtg cgggcccagg accgctacta tagctcatct    960
tggagcgaat gggcatctgt gccctgcagt taggttctga tccagga              1007

<210> SEQ ID NO 2
<211> LENGTH: 900
<212> TYPE: DNA
<213> ORGANISM: Mus musculus

<400> SEQUENCE: 2
cccaaaagag tgacctttga atcatctgta cgcttgccta tgtctagctc agttcatgct     60
gctatcaatc catgagtaag gacctataag cataagagac gccctcaaaa cactatgact    120
tttattagtt attcacctcc ccagagctgt ccctggatac agacaacata ggtatgaggt    180
agggggtacg tggagccaaa caggaggtaa taccttctga atttagatgc taacaagaaa    240
acatggggaa aggtggccca gatacactag gccctttatt ctttgggcct gtaacaccta    300
cttatttgat tgtggcatga accatgaact cggtttgggg caagtccttc cttttttctgc   360 agtctgtgga atcgggagag gttagccatt gccgcctcta ttcaccttag gcatgatgta    420
aacagaaatt agtatctctg cctccttcct ttttccacac cccgaagtca tttcctctta    480
acctgggatt tcgacgtcta tattccctct gtatgataga tgcactcagg gaggcaaggg    540
ggggagggag gaacttctta aaattccccc agaatgtttt gacactagtt ttcagtgttg    600
caattgagac tagtcagttt ctactttggg tttccatcag aaagttctgt aggagtagag    660
tatataagca ccaggagcag ccaaggcagc agaaggaaca gtgggtgtcc aggcacatca    720
gaccaggcag ctcgcagcaa agcaaggtaa gttctctcct cttccctgtc gctaactccc    780
tgcatctaga ggctgtccag attcagactc caggggacag gctaccctg aaccaggcag     840 cgtgggagtg gggtaagtgg attctgggag catctcggat ggctttcccc gctggtggaa    900

<210> SEQ ID NO 3
<211> LENGTH: 328
<212> TYPE: PRT
<213> ORGANISM: human IL-12p40-N222L

<400> SEQUENCE: 3

Met Cys His Gln Gln Leu Val Ile Ser Trp Phe Ser Leu Val Phe Leu
1               5                   10                  15

Ala Ser Pro Leu Val Ala Ile Trp Glu Leu Lys Lys Asp Val Tyr Val
            20                  25                  30

Val

Ser Ser Glu Val Leu Gly Ser Gly Lys Thr Leu Thr Ile Gln Val Lys
65                  70                  75                  80

Glu Phe Gly Asp Ala Gly Gln Tyr Thr Cys His Lys Gly Gly Glu Val
                85                  90                  95

Leu Ser His Ser Leu Leu Leu Leu His Lys Lys Glu Asp Gly Ile Trp
                100                 105                 110

Ser Thr Asp Ile Leu Lys Asp Gln Lys Glu Pro Lys Asn Lys Thr Phe
                115                 120                 125

Leu Arg Cys Glu Ala Lys Asn Tyr Ser Gly Arg Phe Thr Cys Trp Trp
        130                 135                 140

Leu Thr Thr Ile Ser Thr Asp Leu Thr Phe Ser Val Lys Ser Ser Arg
145                 150                 155                 160

Gly Ser Ser Asp Pro Gln Gly Val Thr Cys Gly Ala Ala Thr Leu Ser
                165                 170                 175

Ala Glu Arg Val Arg Gly Asp Asn Lys Glu Tyr Glu Tyr Ser Val Glu
                180                 185                 190

Cys Gln Glu Asp Ser Ala Cys Pro Ala Ala Glu Glu Ser Leu Pro Ile
        195                 200                 205

Glu Val Met Val Asp Ala Val His Lys Leu Lys Tyr Glu Leu Tyr Thr
210                 215                 220

Ser Ser Phe Phe Ile Arg Asp Ile Ile Lys Pro Asp Pro Pro Lys Asn
225                 230                 235                 240

Leu Gln Leu Lys Pro Leu Lys Asn Ser Arg Gln Val Glu Val Ser Trp
                245                 250                 255

Glu Tyr Pro Asp Thr Trp Ser Thr Pro His Ser Tyr Phe Ser Leu Thr
                260                 265                 270

Phe Cys Val Gln Val Gln Gly Lys Ser Lys Arg Glu Lys Lys Asp Arg
        275                 280                 285

Val Phe Thr Asp Lys Thr Ser Ala Thr Val Ile Cys Arg Lys Asn Ala
        290                 295                 300

Ser Ile Ser Val Arg Ala Gln Asp Arg Tyr Tyr Ser Ser Ser Trp Ser
305                 310                 315                 320

Glu Trp Ala Ser Val Pro Cys Ser
                325

<210> SEQ ID NO 4
<211> LENGTH: 328
<212> TYPE: PRT
<213> ORGANISM: human IL-12p40-N222Q

<400> SEQUENCE: 4

Met Cys His Gln Gln Leu Val Ile Ser Trp Phe Ser Leu Val Phe Leu
1               5                   10                  15

Ala Ser Pro Leu Val Ala Ile Trp Glu Leu Lys Lys Asp Val Tyr Val
                20                  25                  30

Val Glu Leu Asp Trp Tyr Pro Asp Ala Pro Gly Glu Met Val Val Leu
                35                  40                  45

Thr Cys Asp Thr Pro Glu Glu Asp Gly Ile Thr Trp Thr Leu Asp Gln
50 55 60

Ser Ser Glu Val Leu Gly Ser Gly Lys Thr Leu Thr Ile Gln Val Lys
65 70 75 80

Glu Phe Gly Asp Ala Gly Gln Tyr Thr Cys His Lys Gly Gly Glu Val
85 90 95

Leu Ser His Ser Leu Leu Leu Leu His Lys Lys Glu Asp Gly Ile Trp

```
                   100                 105                 110
Ser Thr Asp Ile Leu Lys Asp Gln Lys Glu Pro Lys Asn Lys Thr Phe
            115                 120                 125

Leu Arg Cys Glu Ala Lys Asn Tyr Ser Gly Arg Phe Thr Cys Trp Trp
130                 135                 140

Leu Thr Thr Ile Ser Thr Asp Leu Thr Phe Ser Val Lys Ser Ser Arg
145                 150                 155                 160

Gly Ser Ser Asp Pro Gln Gly Val Thr Cys Gly Ala Ala Thr Leu Ser
                165                 170                 175

Ala Glu Arg Val Arg Gly Asp Asn Lys Glu Tyr Glu Tyr Ser Val Glu
            180                 185                 190

Cys Gln Glu Asp Ser Ala Cys Pro Ala Ala Glu Glu Ser Leu Pro Ile
        195                 200                 205

Glu Val Met Val Asp Ala Val His Lys Leu Lys Tyr Glu Gln Tyr Thr
    210                 215                 220

Ser Ser Phe Phe Ile Arg Asp Ile Ile Lys Pro Asp Pro Pro Lys Asn
225                 230                 235                 240

Leu Gln Leu Lys Pro Leu Lys Asn Ser Arg Gln Val Glu Val Ser Trp
                245                 250                 255

Glu Tyr Pro Asp Thr Trp Ser Thr Pro His Ser Tyr Phe Ser Leu Thr
            260                 265                 270

Phe Cys Val Gln Val Gln Gly Lys Ser Lys Arg Glu Lys Lys Asp Arg
        275                 280                 285

Val Phe Thr Asp Lys Thr Ser Ala Thr Val Ile Cys Arg Lys Asn Ala
    290                 295                 300

Ser Ile Ser Val Arg Ala Gln Asp Arg Tyr Tyr Ser Ser Ser Trp Ser
305                 310                 315                 320

Glu Trp Ala Ser Val Pro Cys Ser
                325

<210> SEQ ID NO 5
<211> LENGTH: 335
<212> TYPE: PRT
<213> ORGANISM: mouse IL-12p40-N220L

<400> SEQUENCE: 5

Met Cys Pro Gln Lys Leu Thr Ile Ser Trp Phe Ala Ile Val Leu Leu
1               5                   10                  15

Val Ser Pro Leu Met Ala Met Trp Glu Leu Glu Lys Asp Val Tyr Val
            20                  25                  30

Val Glu Val Asp Trp Thr Pro Asp Ala Pro Gly Glu Thr Val Asn Leu
        35                  40                  45

Thr Cys Asp Thr Pro Glu Glu Asp Asp Ile Thr Trp Thr Ser Asp Gln
    50                  55                  60

Arg His Gly Val Ile Gly Ser Gly Lys Thr Leu Thr Ile Thr Val Lys
65                  70                  75                  80

Glu Phe Leu Asp Ala Gly Gln Tyr Thr Cys His Lys Gly Gly Glu Thr
                85                  90                  95

Leu Ser His Ser His Leu Leu Leu His Lys Lys Glu Asn Gly Ile Trp
            100                 105                 110

Ser Thr Glu Ile Leu Lys Asn Phe Lys Asn Lys Thr Phe Leu Lys Cys
        115                 120                 125

Glu Ala Pro Asn Tyr Ser Gly Arg Phe Thr Cys Ser Trp Leu Val Gln
    130                 135                 140
```

Arg Asn Met Asp Leu Lys Phe Asn Ile Lys Ser Ser Ser Ser Pro
145                 150                 155                 160

Asp Ser Arg Ala Val Thr Cys Gly Met Ala Ser Leu Ser Ala Glu Lys
            165                 170                 175

Val Thr Leu Asp Gln Arg Asp Tyr Glu Lys Tyr Ser Val Ser Cys Gln
        180                 185                 190

Glu Asp Val Thr Cys Pro Thr Ala Glu Glu Thr Leu Pro Ile Glu Leu
    195                 200                 205

Ala Leu Glu Ala Arg Gln Gln Asn Lys Tyr Glu Leu Tyr Ser Thr Ser
    210                 215                 220

Phe Phe Ile Arg Asp Ile Ile Lys Pro Asp Pro Lys Asn Leu Gln
225                 230                 235                 240

Met Lys Pro Leu Lys Asn Ser Gln Val Glu Val Ser Trp Glu Tyr Pro
                245                 250                 255

Asp Ser Trp Ser Thr Pro His Ser Tyr Phe Ser Leu Lys Phe Phe Val
            260                 265                 270

Arg Ile Gln Arg Lys Lys Glu Lys Met Lys Glu Thr Glu Glu Gly Cys
        275                 280                 285

Asn Gln Lys Gly Ala Phe Leu Val Glu Lys Thr Ser Thr Glu Val Gln
    290                 295                 300

Cys Lys Gly Gly Asn Val Cys Val Gln Ala Gln Asp Arg Tyr Tyr Asn
305                 310                 315                 320

Ser Ser Cys Ser Lys Trp Ala Cys Val Pro Cys Arg Val Arg Ser
                325                 330                 335

<210> SEQ ID NO 6
<211> LENGTH: 24
<212> TYPE: DNA
<213> ORGANISM: Artificial Sequence
<220> FEATURE:
<223> OTHER INFORMATION: Primer

<400> SEQUENCE: 6
gtacttaata cgactcacta tagg                                      24

<210> SEQ ID NO 7
<211> LENGTH: 24
<212> TYPE: DNA
<213> ORGANISM: Artificial Sequence
<220> FEATURE:
<223> OTHER INFORMATION: Primer

<400> SEQUENCE: 7
gaagcattaa ccctcactaa aggg                                      24

<210> SEQ ID NO 8
<211> LENGTH: 21
<212> TYPE: DNA
<213> ORGANISM: Artificial Sequence
<220> FEATURE:
<223> OTHER INFORMATION: Primer

<400> SEQUENCE: 8
cccaaacaga aaacgtttct a                                         21

<210> SEQ ID NO 9
<211> LENGTH: 21
<212> TYPE: DNA
<213> ORGANISM: Artificial Sequence
<220> FEATURE:
<223> OTHER INFORMATION: Primer

```
<400> SEQUENCE: 9
cgttttctgt ttgggttctt t                                              21

<210> SEQ ID NO 10
<211> LENGTH: 21
<212> TYPE: DNA
<213> ORGANISM: Artificial Sequence
<220> FEATURE:
<223> OTHER INFORMATION: Primer

<400> SEQUENCE: 10
gccaagcagt attctggacg t                                              21

<210> SEQ ID NO 11
<211> LENGTH: 21
<212> TYPE: DNA
<213> ORGANISM: Artificial Sequence
<220> FEATURE:
<223> OTHER INFORMATION: Primer

<400> SEQUENCE: 11
agaatactgc ttggcctcgc a                                              21

<210> SEQ ID NO 12
<211> LENGTH: 21
<212> TYPE: DNA
<213> ORGANISM: Artificial Sequence
<220> FEATURE:
<223> OTHER INFORMATION: Primer

<400> SEQUENCE: 12
tatgaacagt acaccagcag c                                              21

<210> SEQ ID NO 13
<211> LENGTH: 21
<212> TYPE: DNA
<213> ORGANISM: Artificial Sequence
<220> FEATURE:
<223> OTHER INFORMATION: Primer

<400> SEQUENCE: 13
ggtgtactgt tcatacttga g                                              21

<210> SEQ ID NO 14
<211> LENGTH: 21
<212> TYPE: DNA
<213> ORGANISM: Artificial Sequence
<220> FEATURE:
<223> OTHER INFORMATION: Primer

<400> SEQUENCE: 14
cgcaaacagg ccagcattag c                                              21

<210> SEQ ID NO 15
<211> LENGTH: 21
<212> TYPE: DNA
<213> ORGANISM: Artificial Sequence
<220> FEATURE:
<223> OTHER INFORMATION: Primer

<400> SEQUENCE: 15
gctggcctgt ttgcggcaga t                                              21

<210> SEQ ID NO 16
```

```
<211> LENGTH: 21
<212> TYPE: DNA
<213> ORGANISM: Artificial Sequence
<220> FEATURE:
<223> OTHER INFORMATION: Primer

<400> SEQUENCE: 16
accaagcagg agagttgcct a                                              21

<210> SEQ ID NO 17
<211> LENGTH: 21
<212> TYPE: DNA
<213> ORGANISM: Artificial Sequence
<220> FEATURE:
<223> OTHER INFORMATION: Primer

<400> SEQUENCE: 17
actctcctgc ttggttaatt c                                              21

<210> SEQ ID NO 18
<211> LENGTH: 21
<212> TYPE: DNA
<213> ORGANISM: Artificial Sequence
<220> FEATURE:
<223> OTHER INFORMATION: Primer

<400> SEQUENCE: 18
ataactcagg ggagttgcct g                                              21

<210> SEQ ID NO 19
<211> LENGTH: 21
<212> TYPE: DNA
<213> ORGANISM: Artificial Sequence
<220> FEATURE:
<223> OTHER INFORMATION: Primer

<400> SEQUENCE: 19
actcccctga gttatgaaag a                                              21

<210> SEQ ID NO 20
<211> LENGTH: 21
<212> TYPE: DNA
<213> ORGANISM: Artificial Sequence
<220> FEATURE:
<223> OTHER INFORMATION: Primer

<400> SEQUENCE: 20
tatctgcagg cttcctaaaa a                                              21

<210> SEQ ID NO 21
<211> LENGTH: 21
<212> TYPE: DNA
<213> ORGANISM: Artificial Sequence
<220> FEATURE:
<223> OTHER INFORMATION: Primer

<400> SEQUENCE: 21
ggaagcctgc agatagctca t                                              21

<210> SEQ ID NO 22
<211> LENGTH: 21
<212> TYPE: DNA
<213> ORGANISM: Artificial Sequence
<220> FEATURE:
<223> OTHER INFORMATION: Primer

<400> SEQUENCE: 22
```

```
tatgagctct acagcaccag c                                                    21
```

<210> SEQ ID NO 23
<211> LENGTH: 24
<212> TYPE: DNA
<213> ORGANISM: Artificial Sequence
<220> FEATURE:
<223> OTHER INFORMATION: Primer

<400> SEQUENCE: 23

```
gctgtagagc tcatattttt actg                                                 24
```

<210> SEQ ID NO 24
<211> LENGTH: 335
<212> TYPE: PRT
<213> ORGANISM: Mus musculus

<400> SEQUENCE: 24

```
Met Cys Pro Gln Lys Leu Thr Ile Ser Trp Phe Ala Ile Val Leu Leu
1               5                   10                  15

Val Ser Pro Leu Met Ala Met Trp Glu Leu Glu Lys Asp Val Tyr Val
            20                  25                  30

Val Glu Val Asp Trp Thr Pro Asp Ala Pro Gly Glu Thr Val Asn Leu
        35                  40                  45

Thr Cys Asp Thr Pro Glu Glu Asp Ile Thr Trp Thr Ser Asp Gln
    50                  55                  60

Arg His Gly Val Ile Gly Ser Gly Lys Thr Leu Thr Ile Thr Val Lys
65                  70                  75                  80

Glu Phe Leu Asp Ala Gly Gln Tyr Thr Cys His Lys Gly Gly Glu Thr
                85                  90                  95

Leu Ser His Ser His Leu Leu Leu His Lys Lys Glu Asn Gly Ile Trp
            100                 105                 110

Ser Thr Glu Ile Leu Lys Asn Phe Lys Asn Lys Thr Phe Leu Lys Cys
        115                 120                 125

Glu Ala Pro Asn Tyr Ser Gly Arg Phe Thr Cys Ser Trp Leu Val Gln
    130                 135                 140

Arg Asn Met Asp Leu Lys Phe Asn Ile Lys Ser Ser Ser Pro Pro
145                 150                 155                 160

Asp Ser Arg Ala Val Thr Cys Gly Met Ala Ser Leu Ser Ala Glu Lys
                165                 170                 175

Val Thr Leu Asp Gln Arg Asp Tyr Glu Lys Tyr Ser Val Ser Cys Gln
            180                 185                 190

Glu Asp Val Thr Cys Pro Thr Ala Glu Glu Thr Leu Pro Ile Glu Leu
        195                 200                 205

Ala Leu Glu Ala Arg Gln Gln Asn Lys Tyr Glu Asn Tyr Ser Thr Ser
    210                 215                 220

Phe Phe Ile Arg Asp Ile Ile Lys Pro Asp Pro Lys Asn Leu Gln
225                 230                 235                 240

Met Lys Pro Leu Lys Asn Ser Gln Val Glu Val Ser Trp Glu Tyr Pro
                245                 250                 255

Asp Ser Trp Ser Thr Pro His Ser Tyr Phe Ser Leu Lys Phe Phe Val
            260                 265                 270

Arg Ile Gln Arg Lys Lys Glu Lys Met Lys Glu Thr Glu Glu Gly Cys
        275                 280                 285

Asn Gln Lys Gly Ala Phe Leu Val Glu Lys Thr Ser Thr Glu Val Gln
    290                 295                 300
```

-continued

Cys Lys Gly Gly Asn Val Cys Val Gln Ala Gln Asp Arg Tyr Tyr Asn
305                 310                 315                 320

Ser Ser Cys Ser Lys Trp Ala Cys Val Pro Cys Arg Val Arg Ser
                325                 330                 335

<210> SEQ ID NO 25
<211> LENGTH: 328
<212> TYPE: PRT
<213> ORGANISM: Homo sapiens

<400> SEQUENCE: 25

Met Cys His Gln Gln Leu Val Ile Ser Trp Phe Ser Leu Val Phe Leu
1               5                   10                  15

Ala Ser Pro Leu Val Ala Ile Trp Glu Leu Lys Lys Asp Val Tyr Val
                20                  25                  30

Val Glu Leu Asp Trp Tyr Pro Asp Ala Pro Gly Glu Met Val Val Leu
            35                  40                  45

Thr Cys Asp Thr Pro Glu Glu Asp Gly Ile Thr Trp Thr Leu Asp Gln
    50                  55                  60

Ser Ser Glu Val Leu Gly Ser Gly Lys Thr Leu Thr Ile Gln Val Lys
65                  70                  75                  80

Glu Phe Gly Asp Ala Gly Gln Tyr Thr Cys His Lys Gly Gly Glu Val
                85                  90                  95

Leu Ser His Ser Leu Leu Leu Leu His Lys Lys Glu Asp Gly Ile Trp
            100                 105                 110

Ser Thr Asp Ile Leu Lys Asp Gln Lys Glu Pro Lys Asn Lys Thr Phe
        115                 120                 125

Leu Arg Cys Glu Ala Lys Asn Tyr Ser Gly Arg Phe Thr Cys Trp Trp
    130                 135                 140

Leu Thr Thr Ile Ser Thr Asp Leu Thr Phe Ser Val Lys Ser Ser Arg
145                 150                 155                 160

Gly Ser Ser Asp Pro Gln Gly Val Thr Cys Gly Ala Ala Thr Leu Ser
                165                 170                 175

Ala Glu Arg Val Arg Gly Asp Asn Lys Glu Tyr Glu Tyr Ser Val Glu
            180                 185                 190

Cys Gln Glu Asp Ser Ala Cys Pro Ala Ala Glu Glu Ser Leu Pro Ile
        195                 200                 205

Glu Val Met Val Asp Ala Val His Lys Leu Lys Tyr Glu Asn Tyr Thr
    210                 215                 220

Ser Ser Phe Phe Ile Arg Asp Ile Ile Lys Pro Asp Pro Pro Lys Asn
225                 230                 235                 240

Leu Gln Leu Lys Pro Leu Lys Asn Ser Arg Gln Val Glu Val Ser Trp
                245                 250                 255

Glu Tyr Pro Asp Thr Trp Ser Thr Pro His Ser Tyr Phe Ser Leu Thr
            260                 265                 270

Phe Cys Val Gln Val Gln Gly Lys Ser Lys Arg Glu Lys Lys Asp Arg
        275                 280                 285

Val Phe Thr Asp Lys Thr Ser Ala Thr Val Ile Cys Arg Lys Asn Ala
    290                 295                 300

Ser Ile Ser Val Arg Ala Gln Asp Arg Tyr Tyr Ser Ser Ser Trp Ser
305                 310                 315                 320

Glu Trp Ala Ser Val Pro Cys Ser
                325

What is claimed is:

1. An isolated nucleicacid comprising a mutated human IL-2p40-encoding sequence, wherein the mutated human IL-12p40-encoding sequence comprises the nucleic acid sequence of SEQ ID NO: 1, with the exception that the codon for the amino acid 222 of the encoded IL-12p40 sequence encodes leucine, glutamine or isoleucine.

2. The isolated nucleic acid of claim 1, wherein the mutated IL-12p40 sequence consists of the nucleic acid sequence of SEQ ID NO: 1, with the exception that the codon for the amino acid 222 of the encoded IL-12p40 sequence encodes leucine, glutamine or isoleucine.

3. The isolated nucleic acid of claim 1, wherein said codon for the amino acid 222 is CUC, CAG or AUA.

4. The isolated nucleic acid of claim 3, wherein said codon for the amino acid 222 is CUC.

5. The isolated nucleic acid of claim 3, wherein said codon for the amino acid 222 is CAG.

6. The isolated nucleic acid of claim 1, wherein said codon for the amino acid 222 encodes leucine.

7. The isolated nucleic acid of claim 1, wherein said codon for the amino acid 222 encodes glutamine.

8. The isolated nucleic acid of claim 1, further comprising a human IL-12p35-encoding sequence.

9. The isolated nucleic acid of claim 8, further comprising an IRES operably linked to said mutated human IL-12p40-encoding sequence.

10. The isolated nucleic acid of claim 8, further comprising a promoter operably linked to said human IL-12p35-encoding sequence.

11. The isolated nucleic acid of claim 10, wherein said promoter is a constitutive promoter.

12. The isolated nucleic acid of claim 10, which is expression vector pGX0-hp35/IRES/hp40-N222L.

13. An isolated nucleic acid comprising a mutated mouse IL-12p40-encoding sequence, wherein the mutated mouse IL-12p40-encoding sequence comprises the nucleic acid sequence of SEQ ID NO: 2, with the exception that the codon for the amino acid 220 of the encoded IL-12p40 sequence encodes leucine.

14. The isolated nucleic acid of claim 13, further comprising a mouse IL-12p35-encoding nucleic acid.

15. The isolated nucleic acid of claim 14, further comprising an IRES operably linked to said mouse IL-12p40-encoding nucleic acid.

16. The isolated nucleic acid of claim 14, further comprising a promoter operably linked to said mouse IL-12p35-encoding nucleic acid.

17. The isolated nucleic acid of claim 16, wherein said promoter is a constitutive promoter.

18. The isolated nucleic acid of claim 16, which is a therapeutic or prophylactic adjuvant expression vector for DNA immunization.

19. The isolated nucleic acid of claim 18, wherein said expression vector is pTV2-mp35/IRES/mp40-N220L.

* * * * *

UNITED STATES PATENT AND TRADEMARK OFFICE
CERTIFICATE OF CORRECTION

PATENT NO.        : 7,253,151 B2                                Page 1 of 1
APPLICATION NO.   : 10/221975
DATED             : August 7, 2007
INVENTOR(S)       : Young Chul Sung et al.

It is certified that error appears in the above-identified patent and that said Letters Patent is hereby corrected as shown below:

Col. 45, line 3,
Replace "IL-2p40" with --IL-12p40--.

Signed and Sealed this

Fourth Day of May, 2010

David J. Kappos
*Director of the United States Patent and Trademark Office*